United States Patent
Prillinger et al.

(10) Patent No.: US 10,981,001 B2
(45) Date of Patent: Apr. 20, 2021

(54) SYSTEMS AND METHODS FOR AUTOMATED CAPTURE THRESHOLD TESTING AND ASSOCIATED HIS BUNDLE PACING

(71) Applicant: PACESETTER, INC., Sylmar, CA (US)

(72) Inventors: Julie Prillinger, Redwood City, CA (US); Gene A. Bornzin, Simi Valley, CA (US); Stuart Rosenberg, Castaic, CA (US); Aditya Goil, Stevenson Ranch, CA (US); Wenwen Li, San Jose, CA (US); Pritika Toutam, Winnetka, CA (US); Didier Theret, Porter Ranch, CA (US); Fujian Qu, San Jose, CA (US)

(73) Assignee: PACESETTER, INC., Sylmar, CA (US)

(*) Notice: Subject to any disclaimer, the term of this patent is extended or adjusted under 35 U.S.C. 154(b) by 612 days.

(21) Appl. No.: 15/653,357

(22) Filed: Jul. 18, 2017

(65) Prior Publication Data
US 2019/0022378 A1    Jan. 24, 2019

(51) Int. Cl.
*A61N 1/37* (2006.01)
*A61N 1/05* (2006.01)
(Continued)

(52) U.S. Cl.
CPC .......... *A61N 1/0565* (2013.01); *A61N 1/056* (2013.01); *A61N 1/3621* (2013.01);
(Continued)

(58) Field of Classification Search
CPC .... A61N 1/362; A61N 1/3621; A61N 1/3622; A61N 1/3627; A61N 1/365;
(Continued)

(56) References Cited

U.S. PATENT DOCUMENTS 3,524,442 A * 8/1970 Horth .................. A61B 5/0456
600/516
3,920,024 A * 11/1975 Bowers ................ A61N 1/3712
607/28

(Continued)

OTHER PUBLICATIONS

Deshmukh et al. "Permanent, Direct His-Bundle Pacing: A Novel Approach to Cardiac Pacing in Patients With Normal His-Purkinje Activation". Circulation. Feb. 2, 2000; 101 (8):869-77.*

(Continued)

*Primary Examiner* — Eugene T Wu
(74) *Attorney, Agent, or Firm* — The Small Patent Law Group LLC; Dean D. Small

(57) ABSTRACT

A method of pacing a His bundle of a patient heart using a stimulation system including a memory, a pulse generator, a stimulating electrode and at least one sensing electrode includes applying a plurality of impulses through the stimulating electrode to induce a plurality of responses from the patient heart. Each impulse of the plurality of impulses is delivered at a different impulse energy corresponding to a respective output setting of the stimulation system. The response characteristics for each of the plurality of responses are measured and each impulse is assigned a classification based on whether the respective response characteristics indicate capture of one or both of the His bundle and a ventricle of the patient heart. The output setting and classification for each impulse is then stored in the memory.

21 Claims, 13 Drawing Sheets

(51) Int. Cl.
*A61N 1/362* (2006.01)
*A61N 1/39* (2006.01)
*A61N 1/368* (2006.01)
*A61N 1/38* (2006.01)
*A61N 1/08* (2006.01)

(52) U.S. Cl.
CPC ............ *A61N 1/3627* (2013.01); *A61N 1/37* (2013.01); *A61N 1/371* (2013.01); *A61N 1/3712* (2013.01); *A61N 1/3956* (2013.01); *A61N 1/3962* (2013.01); *A61N 1/3686* (2013.01); *A61N 1/385* (2013.01); *A61N 2001/083* (2013.01)

(58) Field of Classification Search
CPC ....... A61N 1/36507; A61N 1/37; A61N 1/371; A61N 1/3712; A61B 5/0468; A61B 5/0472
See application file for complete search history.

(56) References Cited

U.S. PATENT DOCUMENTS

| | | | | |
|---|---|---|---|---|
| 4,686,988 A | * | 8/1987 | Sholder | A61N 1/365 600/510 |
| 2011/0264158 A1 | * | 10/2011 | Dong | A61B 5/7264 607/9 |
| 2012/0239106 A1 | * | 9/2012 | Maskara | A61N 1/3627 607/28 |
| 2014/0107724 A1 | * | 4/2014 | Shuros | A61N 1/3712 607/28 |

OTHER PUBLICATIONS

Vijayaraman et al. "Permanent His bundle pacing: Recommendations from a Multicenter His Bundle Pacing Collaborative Working Group for standardization of definitions, implant measurements, and follow-up". Heart Rhythm. Mar. 15, 2018(3):460-468. doi: 10.1016/j.hrthm.2017.10.039. Epub Oct. 2, 2017.*

His-Pacing.org. <http://www.his-pacing.org/the-list-his-bundle-pacing-papers/>. Accessed Sep. 21, 2019.*

Cantu et al. "Validation of criteria for selective his bundle and para-hisian permanent pacing". Pacing Clin Electrophysiol. Dec. 29, 2006(12):1326-33.*

* cited by examiner

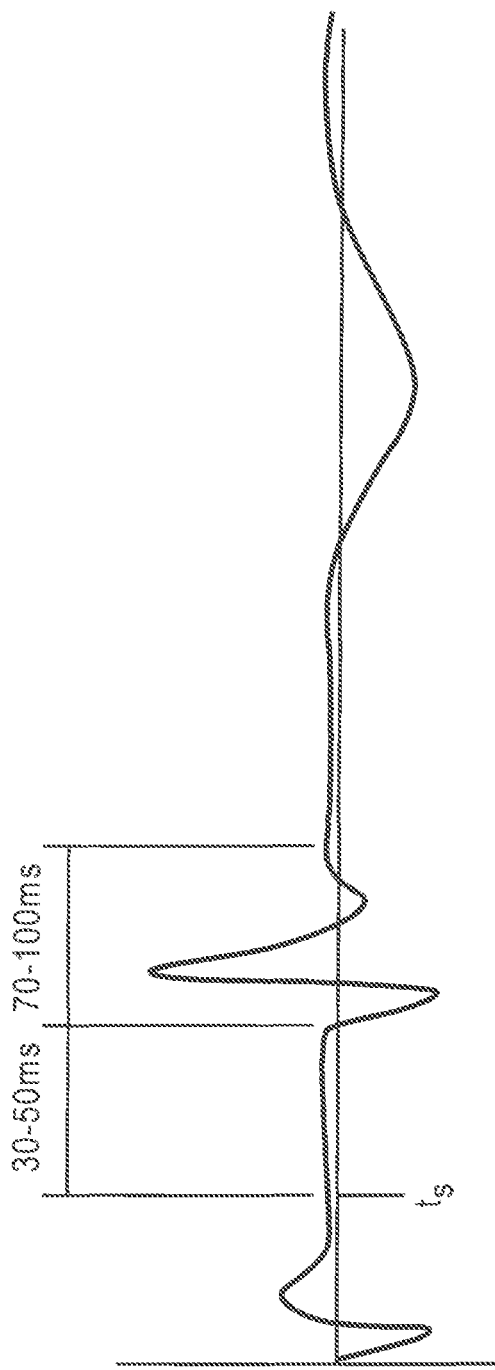
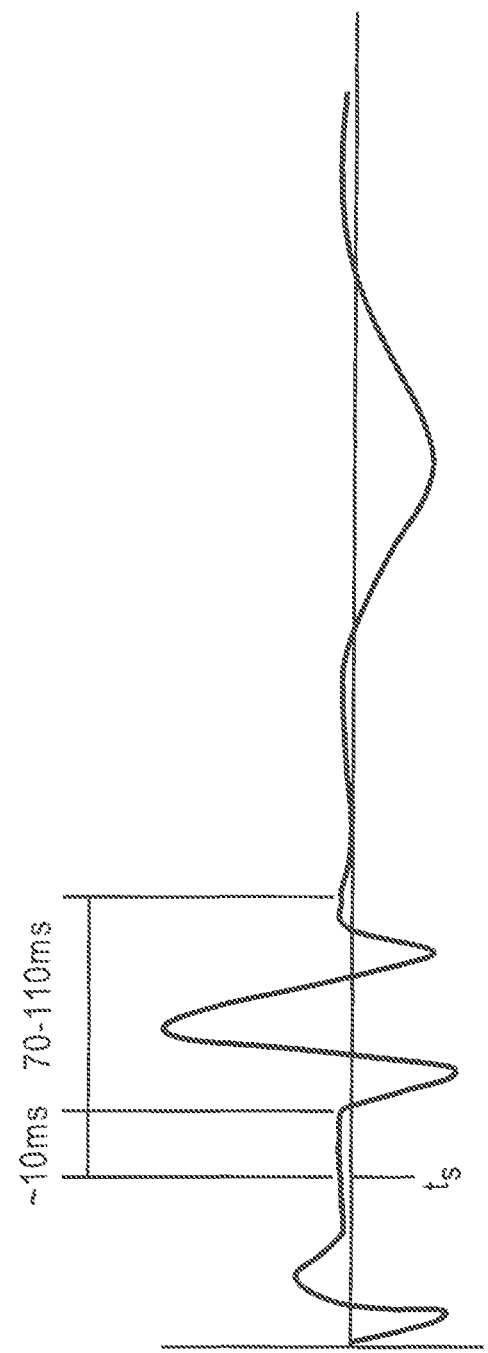

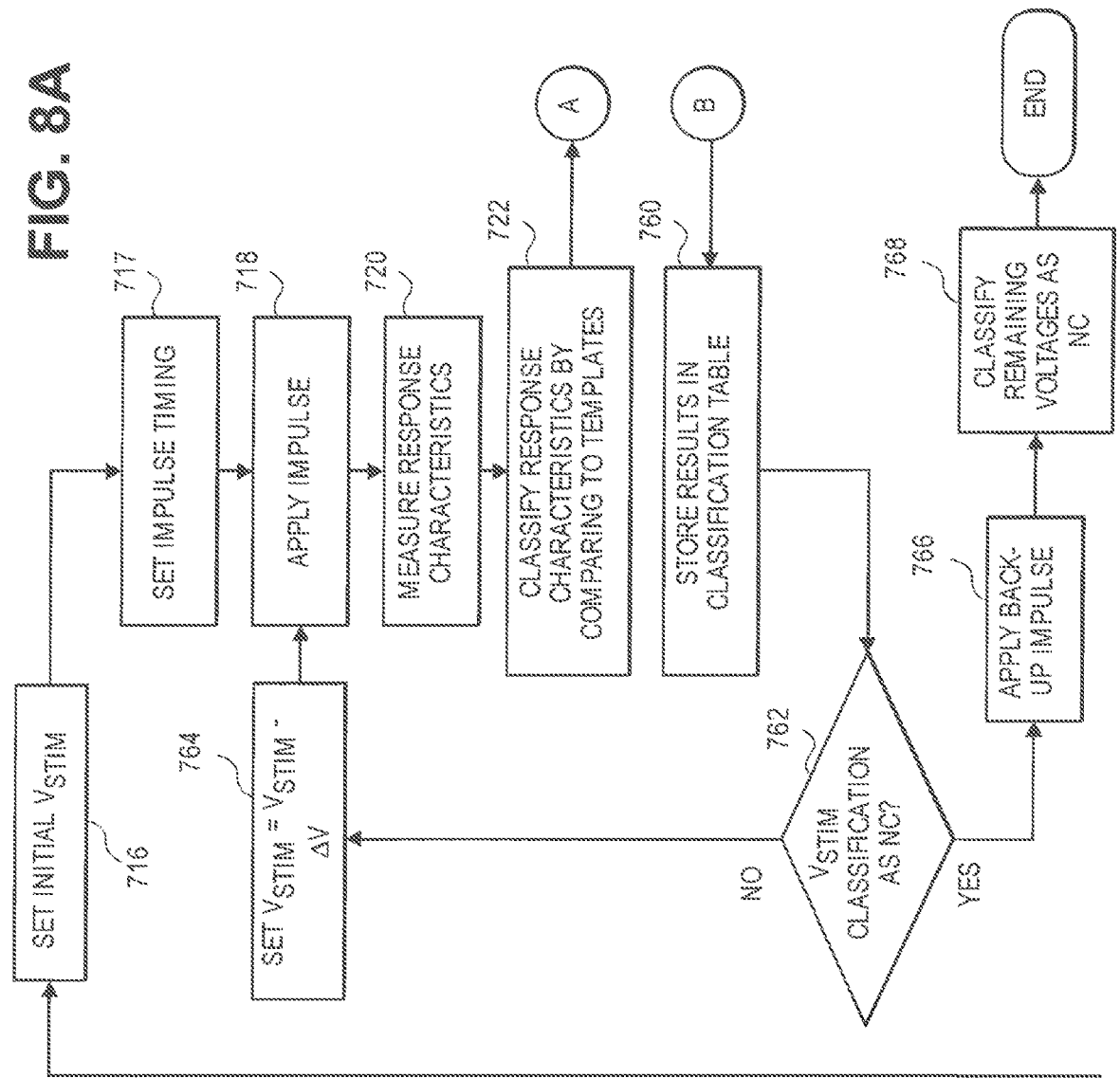
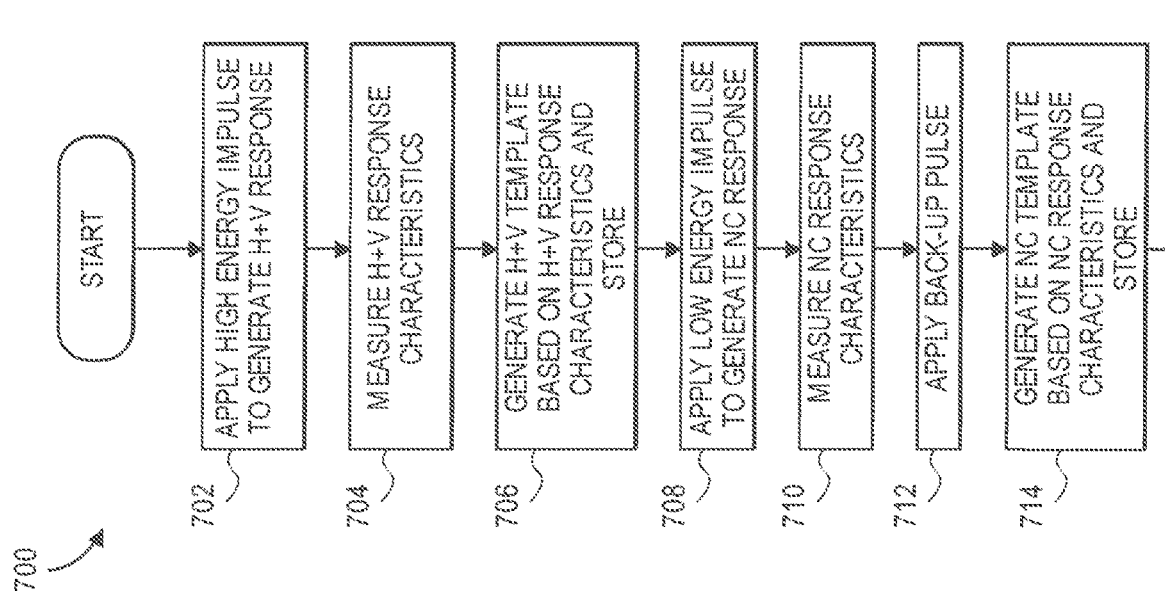
FIG. 8A

SYSTEMS AND METHODS FOR AUTOMATED CAPTURE THRESHOLD TESTING AND ASSOCIATED HIS BUNDLE PACING

FIELD

This disclosure relates generally to implantable cardiac stimulating devices. More specifically, the present disclosure is directed to a cardiac stimulation device that includes a lead for His bundle pacing and that includes logic for automatically identifying and implementing settings of the cardiac stimulation device for delivering His bundle pacing. This disclosure further relates to a method for identifying and implementing cardiac stimulating device settings for His bundle pacing.

BACKGROUND

In a normal human heart, the sinus node, generally located near the junction of the superior vena cava and the right atrium, constitutes the primary natural pacemaker initiating rhythmic electrical excitation of the heart chambers. The cardiac impulse arising from the sinus node is transmitted to the two atrial chambers, causing a depolarization known as a P-wave and the resulting atrial chamber contractions. The excitation pulse is further transmitted to and through the ventricles via the atrioventricular (AV) node and a ventricular conduction system comprised of the bundle of His (also referred to as the His bundle), the left and right bundle branches, and the Purkinje fibers, causing a depolarization and the resulting ventricular chamber contractions. The depolarization of the interventricular septum and ventricles is generally referred to as a QRS complex and is observed and measured through the use of electrocardiograms (ECGs) and similar equipment for measuring electrical activity of the heart.

Disruption of this natural pacemaking and conduction system as a result of aging or disease can be successfully treated by artificial cardiac pacing using implantable cardiac stimulation devices, including pacemakers and implantable defibrillators, which deliver rhythmic electrical pulses or other anti-arrhythmia therapies to the heart, via electrodes implanted in contact with the heart tissue, at a desired energy and rate. To the extent the electrical pulses are sufficient to induce depolarization of the associated heart tissue, the heart tissue is said to be captured and the minimum electrical pulse resulting in capture is generally referred to as the capture threshold.

In the majority of individuals, the most effective heartbeat is triggered by the patient's own natural pacing physiology. Implantable cardiac stimulation devices are intended to fill in when the natural pacing functionality of the patient's heart falls or acts inefficiently (such as in cases of sinus arrest and symptomatic bradycardia, respectively) or when the heart's conduction system fails or acts inefficiently (such as in cases of third-degree and second-degree (i.e., Mobitz II) AV blocks, respectively). In a large number of heart failure patients, natural conduction through the AV node and the His bundle are intact and disruption of ventricular rhythm is the result of conduction disorders residing in the left and/or right bundle branches.

Dilatation of the heart due to congestive heart failure (CNF) has been associated with delayed conduction through the ventricles. This delayed conduction leads to reduced hemodynamic efficiency of the failing heart because of the resulting poor synchronization of the heart chambers.

Direct stimulation of the His bundle has been found to provide hemodynamic improvement for various patients including those suffering from dilated cardiomyopathy but having normal ventricular activation. Other examples of patients that may benefit from direct stimulation of the His bundle include those with atrioventricular junction (AVJ) ablation or third-degree AV block that require permanent ventricular pacing. Accordingly, the natural conduction system, when intact, can provide hemodynamically optimal depolarization timing of the heart chambers.

What is needed, therefore, is a cardiac stimulation device capable of identifying electrical pulses for inducing His bundle capture and self-configuring output settings of the cardiac stimulation device to output such electrical pulses. To improve efficiency and operational life of the cardiac stimulation device, it would be desirable that the cardiac stimulation device identify the minimum power and rate necessary to induce His bundle capture and subsequent ventricular depolarization.

BRIEF SUMMARY OF THE DISCLOSURE

Disclosed herein are methods and systems for providing His bundle pacing of a patient heart. The methods and systems include performing automated capture threshold testing to determine impulse energies to most efficiently pace the patient heart, initializing a stimulation system in accordance with the automated capture threshold testing, and continuously monitoring response characteristics of the patient heart to ensure proper pacing is maintained.

For example, a method of pacing of a His bundle of a patient heart using a stimulation system is provided, the stimulation system including a memory, a pulse generator, a stimulating electrode disposed in proximity to the His bundle, and at least one sensing electrode adapted to sense electrical activity of the patient heart. The method includes applying a plurality of impulses to induce a plurality of responses from the patient heart, each impulse having a different impulse energy corresponding to a respective output setting of the stimulation system. The method further includes measuring response characteristics for each of the plurality of responses using the sensing electrode. Each impulse is assigned a classification based on whether the respective response characteristics indicate capture of one, both, or neither of the His bundle and a ventricle of the patient heart. Finally, each of the output setting and the classification associated with the impulse are stored in the memory.

In one embodiment, the response characteristics include each of a QRS complex duration and an evoked response delay. In one embodiment, the output setting of the stimulation system includes at least one of a stimulation voltage and an impulse duration.

In one embodiment, the method further includes generating and storing templates corresponding to values that indicate capture of particular cardiac tissue. In such embodiments, assigning a classification to an impulse include comparing the response characteristics corresponding to the impulse to one or more of the stored templates. In certain embodiments, the templates may include templates corresponding to selective His bundle capture (i.e., capture of the His bundle only), non-selective His bundle capture (i.e., capture of the His bundle and other cardiac tissue, such as the right ventricle), ventricle-only capture, and non-capture of the His bundle and ventricle. Generating the templates may include applying predetermined impulses selected to capture specific cardiac tissue, measuring corresponding response characteristics, and assigning a value or range of values to a template based on the response characteristics.

In one embodiment the memory includes an ordered table arranged in order of impulse energy and storing the output settings and classifications includes generating a corresponding record in the ordered table.

In one embodiment, the method further includes configuring the output settings of the stimulation system. Configuring the output settings further includes identifying a lowest-energy impulse that resulted in capture of the His bundle or, if no impulse is classified as such, of the ventricle. The output settings corresponding to the lowest-energy impulse are then retrieved from the memory and the output settings of the stimulation system are configured based on the retrieved output settings. In certain embodiments, the output settings of the stimulation system correspond to the stored output settings augmented by a safety factor.

In one embodiment, a back-up impulse is applied in the event an impulse is classified as resulting in non-capture of the His bundle and the ventricle. The back-up impulse is generally an impulse having sufficient energy to capture at least one of the His bundle and the ventricle.

As another example, a second method of pacing a His bundle of a patient heart using a stimulation system is provided, the stimulation system Including a memory, a pulse generator, a stimulating electrode disposed in proximity to the His bundle, and at least one sensing electrode adapted to sense electrical activity of the patient heart. The method includes initializing one or more output settings of the stimulation system. Initialization further includes accessing a table stored in the memory that includes entries including respective output settings and classifications. The classifications indicate whether the output settings resulted in capture of one or both of the His bundle and a ventricle of the patient heart. Initialization further includes identifying a lowest-energy output setting from the table and configuring the output settings of the stimulation device based on the lowest-energy output setting. An impulse is then applied to the patient heart using the output settings.

In one embodiment, the method further includes measuring response characteristics of the patient heart resulting from application of the impulse. A determination is then made as to whether the response characteristics indicate capture or non-capture of heart tissue that is inconsistent with the classification of the lowest-energy output setting. If such an inconsistency is present, the output settings are modified to increase the energy of a subsequent impulse. The determination is made, in some embodiments, by comparing the response characteristics to a template stored in the memory that corresponds to the classification of the lowest-energy output setting. In certain embodiments, modifying the output settings may include at least one of increasing a voltage setting or increasing an impulse duration setting of the stimulation system. In other embodiments, modifying the output settings may include identifying a second output setting from the table having a higher energy than the lowest-energy output setting. The output setting of the stimulation device is then set to the second output setting or an intermediate output setting between the lowest-energy output setting and the second output setting.

As yet another example, a cardiac stimulation system is provided. The cardiac stimulation system is adapted to deliver impulses for pacing a His bundle of a patient heart using a stimulation electrode and to sense response characteristics of the His bundle and a ventricle of the patient heart using one or more sensing electrodes in response to impulses delivered by the stimulation electrode. The stimulation system further includes a pulse generator adapted to generate electrical impulses for pacing the His bundle and a processor communicatively coupled to the pulse generator and adapted to receive response characteristics from the one or more sensing electrodes. The stimulation system also includes a memory communicatively coupled to the processor. The memory includes instructions that, when executed by the processor, cause the processor to generate a plurality of impulses to induce responses from the patient heart, each impulse corresponding to a different output setting of the pulse generator. The processor further receives response characteristics for each response and assigns classifications based on the response characteristics to each of the impulses based on whether capture of the His bundle and/or ventricle occurred. The processor then stores the output settings and classifications in the memory.

In one embodiment, the instructions further cause the processor to identify a lowest-energy impulse and to set an output of the pulse generator based on the output settings associated with the lowest-energy impulse. The lowest-energy impulse is generally that which resulted in capture of at least the His bundle or, if no such impulse exists, in capture of the ventricle. In certain embodiments, identifying the lowest-energy impulse includes accessing a table stored in the memory, the table including entries that include an output setting and a corresponding classification. The instructions may further cause the processor to apply an impulse based on the output settings, receive response characteristics corresponding to the impulse, and determine whether the response characteristics are inconsistent with the classification associated with the output settings. If such an inconsistency exists, the output settings may be modified to have an increased energy.

In one embodiment, the response characteristics include each of a QRS complex duration and an evoked response delay.

In one embodiment, the cardiac stimulation system further includes at least one stimulation electrode electrically coupled to the pulse generator by a stimulation electrode lead and at least one sensing electrode electrically coupled to the processor by a sensing electrode lead. The stimulation electrode is adapted to deliver impulses generated by the pulse generator to the patient heart. The sensing electrode is adapted to sense response characteristics of the His bundle and the ventricle in response to impulses delivered by at least one stimulation electrode and to deliver the sensed response characteristics to the processor.

BRIEF DESCRIPTION OF THE DRAWINGS

The various features of the present disclosure and the manner of attaining them will be described in greater detail with reference to the following description, claims, and drawings, wherein reference numerals are reused, where appropriate, to indicate a correspondence between the referenced items, and wherein:

FIGS. 1A and 1B are example electrocardiograms illustrating selective and non-selective His bundle capture, respectively;

FIGS. 8A and 8B are a flow chart illustrating a method of performing a capture threshold test that may be implemented using the stimulation device of FIG. 2;

DETAILED DESCRIPTION

Figure 2:
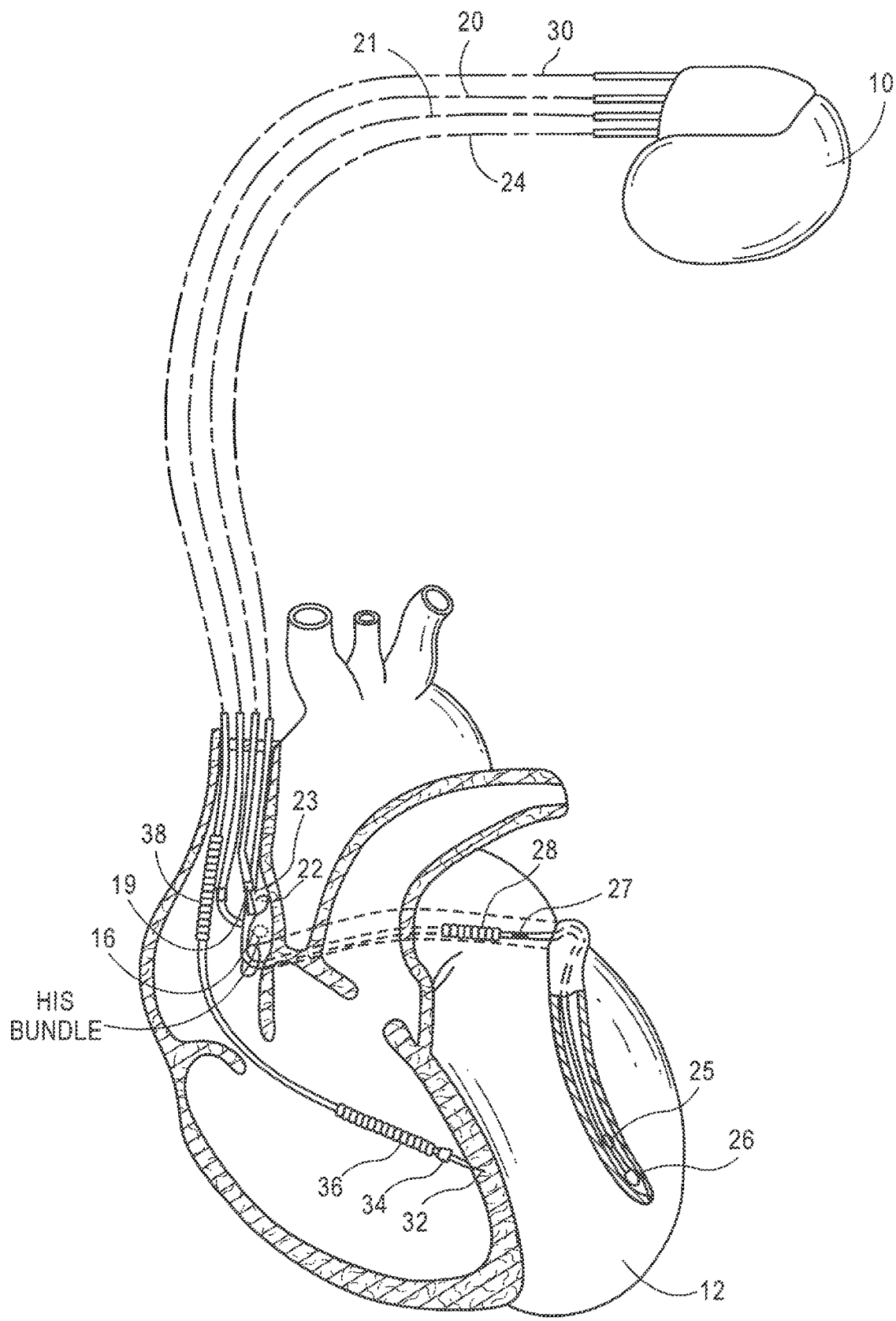
FIG. 2 is a simplified, partly cutaway view illustrating an implantable stimulation device in electrical communication with at least four leads, including a His Bundle lead, implanted into a patient's heart for delivering multi-chamber stimulation and shock therapy.

The present disclosure is directed at providing a method and apparatus for automatic determination of His bundle capture thresholds and for configuring stimulation devices based on the determined capture thresholds. One embodiment of the present disclosure may be implemented in either a dual chamber or multi-chamber cardiac stimulation device. For example, the present disclosure may be implemented in a rate-responsive multi-chamber cardiac stimulation device such as the stimulation device 10 depicted in FIG. 2.

Certain cardiac pacemakers and defibrillators incorporate a pacing lead in the right ventricle and may also include a second lead in the right atrium. High-burden right ventricle pacing may contribute to the development of pacing-induced cardiomyopathy and symptoms associated with heart failure (HF). Several pathophysiologic mechanisms have been implicated in the development of pacing-induced HF, each of which likely stems from non-physiological electrical and mechanical activation patterns produced by right ventricle pacing. His bundle pacing (HBP) may restore physiological activation patterns by utilizing a patient's intrinsic conduction system and may do so even in the presence of bundle branch block. HBP has also been shown to provide significant QRS narrowing, with improved election fraction.

Another possible clinical application of HBP is cardiac resynchronization therapy (CRT). Conventional CRT systems include pacing from both a right ventricular and a left ventricular lead, and have been shown most effective for patients exhibiting a wide QRS complex and left bundle branch block. HBP has also been shown to be effective at narrowing the QRS complex in patients with left bundle branch block, likely due to the anatomy of the His bundle, which includes right and left bundle fibers that are longitudinally dissociated. Therefore, what is thought of as left bundle branch block, can be a result of a proximal blockage within the His bundle that eventually branches to the left bundle. As a result, by pacing the His bundle distal to the blockage, a normalized QRS complex can be achieved in some patients. Theoretically, this pacing mode may provide even better results than known CRT treatments, as activation propagates rapidly through natural conduction pathways.

The His bundle is a narrow cluster of cardiac muscle fibers that passes electrical impulses from the AV node to the interventricular septum. It is anatomically located adjacent to the annulus of the tricuspid valve, inferior to or within the membranous septum. During normal functioning of the heart, the delay between excitation of the His bundle and a subsequent depolarization of the ventricles in response to the excitation is generally on the order of approximately 30-50 milliseconds (ms) and the resulting QRS complex generally has a duration of approximately 70-100 ms.

Depending on electrode position, pacing leads targeted for the His bundle may achieve either non-selective or selective HBP. Non-selective His bundle pacing (nsHBP) refers to pacing of the His bundle in which both the His bundle and the local myocardium surrounding the His bundle are captured. Capture occurs when an electrical stimulus applied to the heart is of sufficient energy to depolarize the cardiac tissue, thereby causing the heart muscle to contract. As a result of the simultaneous depolarization of multiple areas of cardiac tissue, the sequential electrical responses typically observed during normal heart activity may be combined or condensed. His bundle capture resulting in such a response is often characterized by the stimulus to ventricular depolarization duration being short, on the order of 20 ms, because the myocardial depolarization propagates immediately without exclusively traveling through the His-Purkinje system. Because the His bundle is stimulated, the QRS duration is similar to the native QRS duration but may be slightly longer due to the myocardial excitation (e.g., 70-120 ms). In contrast, selective His bundle pacing (sHBP) refers to exclusive capture of the His bundle without stimulating surrounding myocardial tissue. With sHBP, the stimulus to ventricular depolarization interval is virtually the same as the native delay between His bundle stimulation and subsequent ventricular depolarization and the QRS duration is essentially identical to the native QRS duration.

To further illustrate the foregoing, FIGS. 1A and 1B are example electrocardiograms corresponding to selective and non-selective His bundle capture, respectively. In each of FIGS. 1A and 1B, a stimulus is applied at a predetermined time ($t_s$) following an atrial event. In FIG. 1A, selective His bundle capture occurs, i.e., only the His bundle is captured and the myocardium is not excited by the stimulus applied at $t_s$. As a result, the delay between application of the stimulus and initiation of the QRS complex is generally in the range of approximately 30 to 50 ms, which is generally consistent with normal heart function. The resulting QRS may be narrowed, but is typically between 70 and 100 ms in duration. The example electrocardiogram of FIG. 1B, in contrast, illustrates non-selective His bundle capture in which the stimulus applied at $t_s$ results in simultaneous capture of both the His bundle and the myocardium. With non-selective capture the delay between application of the stimulus and the initiation of the QRS complex is reduced (typically less than 10 ms) and the QRS duration generally remains between 70 and 120 ms.

Because sHBP more closely approximates native heart function, if is generally preferred to nsHBP. However, due to the complexity and dynamic nature of certain cardiomyopathies and cardiac anatomies, sHBP may not be possible or, if possible at one time, may no longer be possible as a patient's condition changes. Moreover, a patient's condition may also change to the point where HBP is generally unsuitable as a pacing method and ventricular pacing is required.

Figure 11:
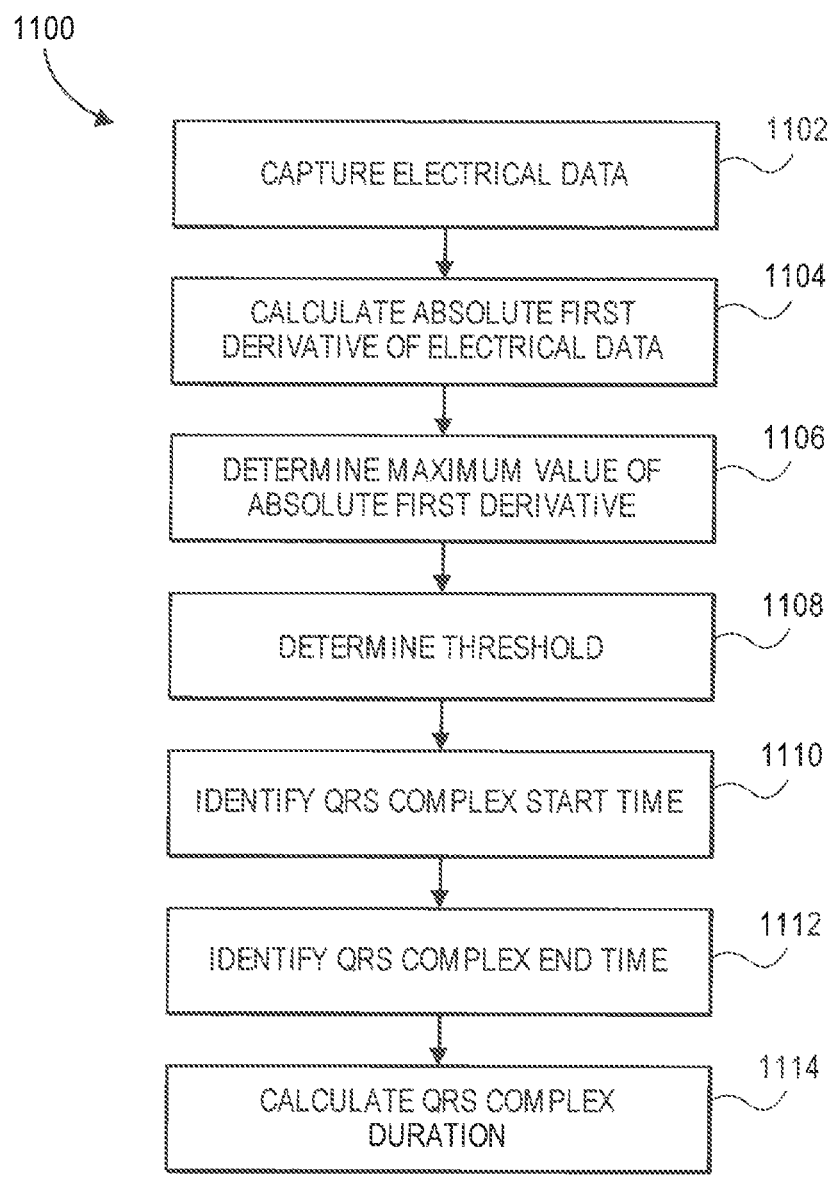
FIG. 11 is a flow chart illustrating a method for determining QRS complex duration.
Figure 12A:
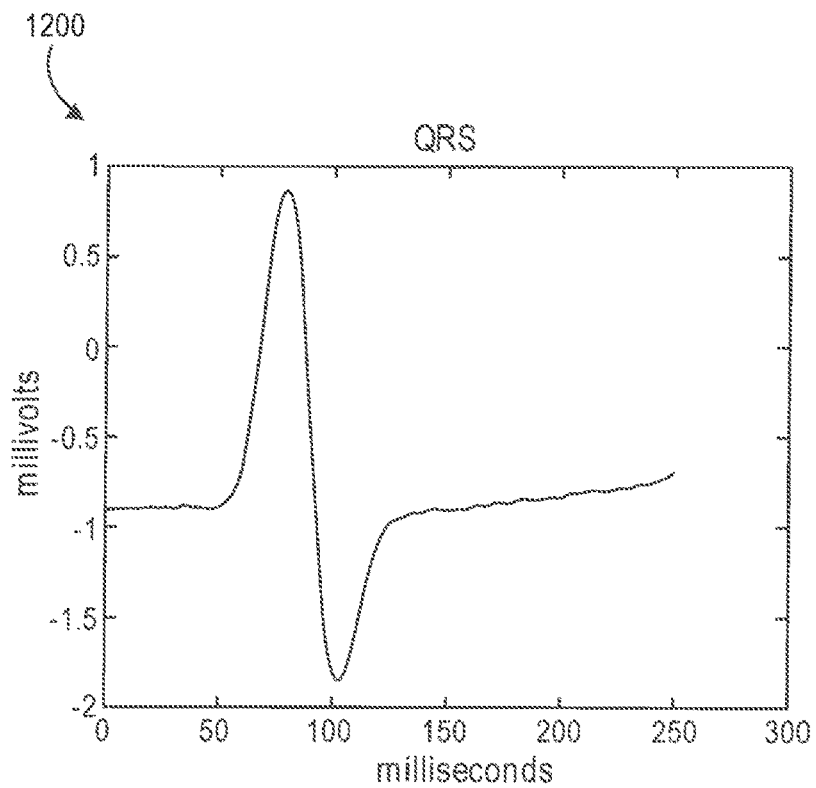
FIGS. 12A and 12B are graphs of example electrical data for illustrating the method of FIG. 11.
Figure 12B:
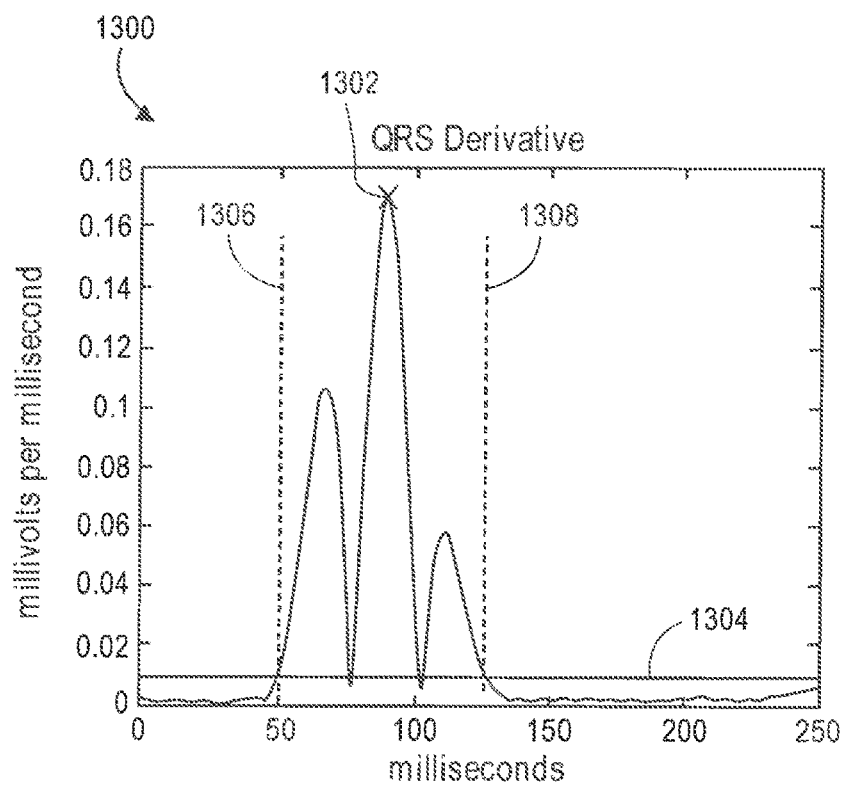

In light of the foregoing, this disclosure describes methods and apparatuses directed to optimizing HBP of a patient's heart. More specifically, this disclosure describes stimulation devices capable of HBP and processes that may be implemented by such stimulation devices to initialize and dynamically modify settings of the stimulation devices to provide HBP. To do so, the stimulation devices are generally capable of identifying and dynamically modifying one or more capture thresholds associated with HBP. As discussed below in more details, FIGS. 2-7 generally describe the components and functionality of stimulation devices in accordance with this disclosure while FIGS. 8A-10 illustrate various processes that may be implemented by such stimulation devices to provide HBP. FIGS. 11 and 12A-B illustrate a method for determining QRS duration in accordance with this disclosure as may be used during the methods of FIGS. 8A-10.

With reference to FIG. 2, the stimulation device 10 is shown in electrical communication with a patient's heart 12 byway of four leads, 20, 21, 24, and 30 and suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage or atrial septum.

To sense left atrial and ventricular cardiac signals and to provide left chamber pacing therapy, the stimulation device 10 is coupled to a "coronary sinus" lead 24 designed for placement in the "coronary sinus region" via the coronary sinus ostium for positioning a distal electrode within the coronary veins overlying the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus which overlies the left ventricle.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28. In another embodiment, an additional electrode for providing left ventricular defibrillation shocking therapy may be included in the portion of the lead overlying the left ventricle, adjacent to the ring electrode 25.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular coil electrode 36, and a superior vena cava (SVC) coil electrode 38. Typically, the right ventricular lead 30 is transvenously inserted into the heart 12 so as to place the right ventricular tip electrode 32 in the right ventricular apex so that the right ventricular coil electrode 36 will be positioned in the right ventricle and the SVC coil electrode 38 will be positioned in the superior vena cava. Accordingly, the right ventricular lead 30 is capable of receiving cardiac signals and delivering stimulation in the form of pacing and shock therapy to the right ventricle.

The stimulation device 10 is further connected to a His bundle lead 21 having a His tip electrode 16, such as a helical active fixation device, and a His ring electrode 19 located proximal from the His tip electrode 16. In certain implementations, the His ring electrode 19 is located approximately 10 mm proximal the His tip electrode 16. The His bundle lead 21 may be transvenously inserted into the heart 12 so that the His tip electrode 16 is positioned in the tissue of the His bundle. Accordingly, the His bundle lead 21 is capable of receiving depolarization signals propagated in the His bundle or delivering stimulation to the His bundle, creating a depolarization that can be propagated through the lower conductive pathways of the right and left ventricles (i.e., the right and left bundle branches and Purkinje fibers).

The His bundle lead 21 will be described in greater detail in conjunction with FIGS. 5 and 6.

Figure 3:
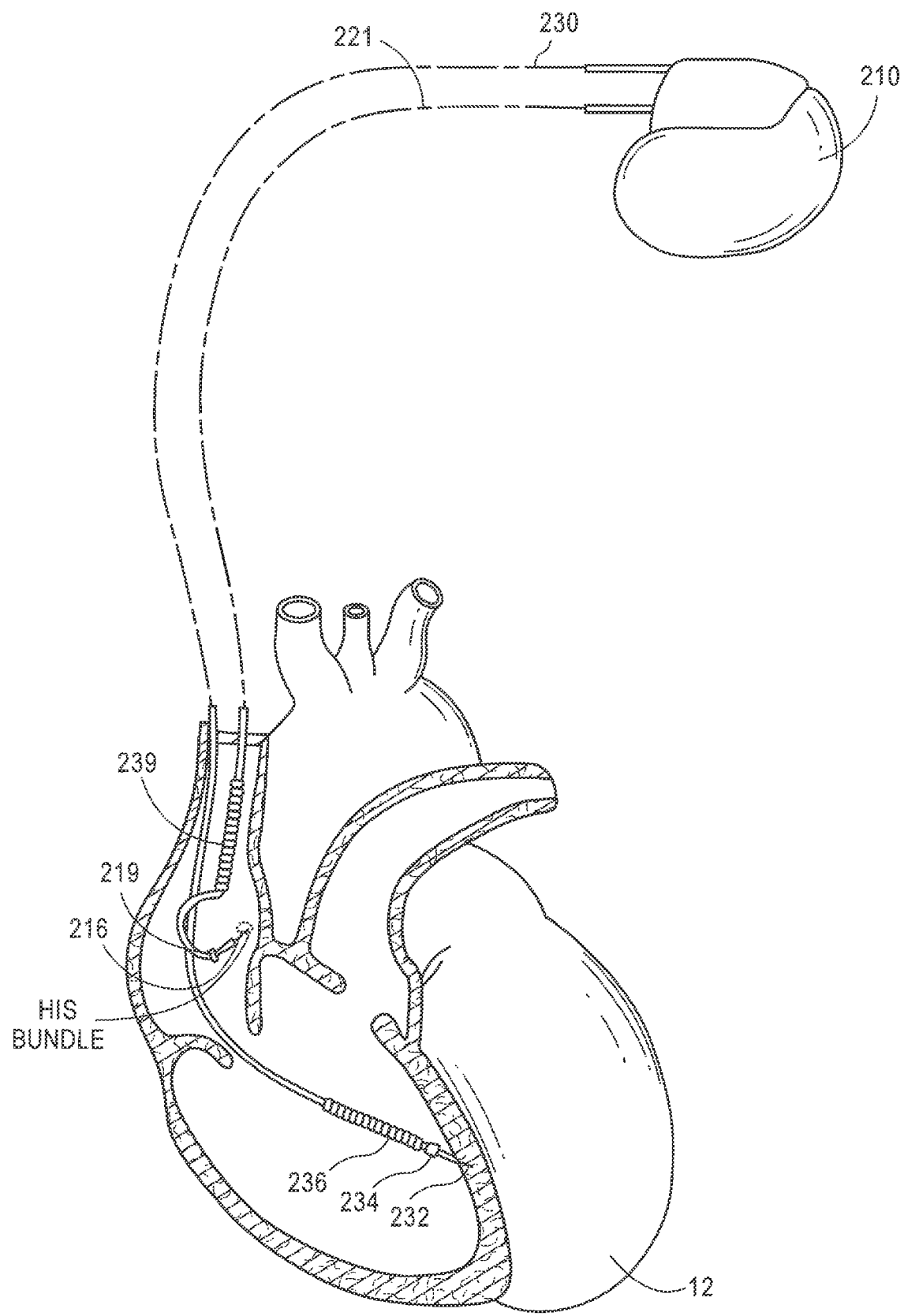
FIG. 3 is a simplified, partly cutaway view illustrating an alternative design of an implantable stimulation device, shown implanted into the right chambers of the patient's heart for delivering dual-chamber stimulation and shock therapy.

An alternative embodiment of the present disclosure is shown in FIG. 3 in which a dual chamber stimulation device 210 is in communication with one atrium, one ventricle, and the His bundle. Though not explicitly illustrated in FIG. 3, a right atrial lead 20 (shown in FIG. 2) can be optionally included. In such implementations, the stimulation device 210 maintains communication with the right atrium of the heart 12 via a right atrial lead 20 having at least an atrial tip electrode 22 and an atrial ring electrode 23 (which may be implanted in the patient's right atrial appendage as described earlier in connection with FIG. 2), and an SVC coil electrode 239.

A His bundle lead 221, having a His tip electrode 216 and a His ring electrode 219, is positioned such that the His tip electrode 216 is proximate the His bundle tissue. The stimulation device 210 is shown in FIG. 3 in electrical communication with the patient's heart 12 by way of a right ventricular lead 230 including a right ventricular tip electrode 232, a right ventricular ring electrode 234, and a right ventricular coil electrode 236.

Figure 4:
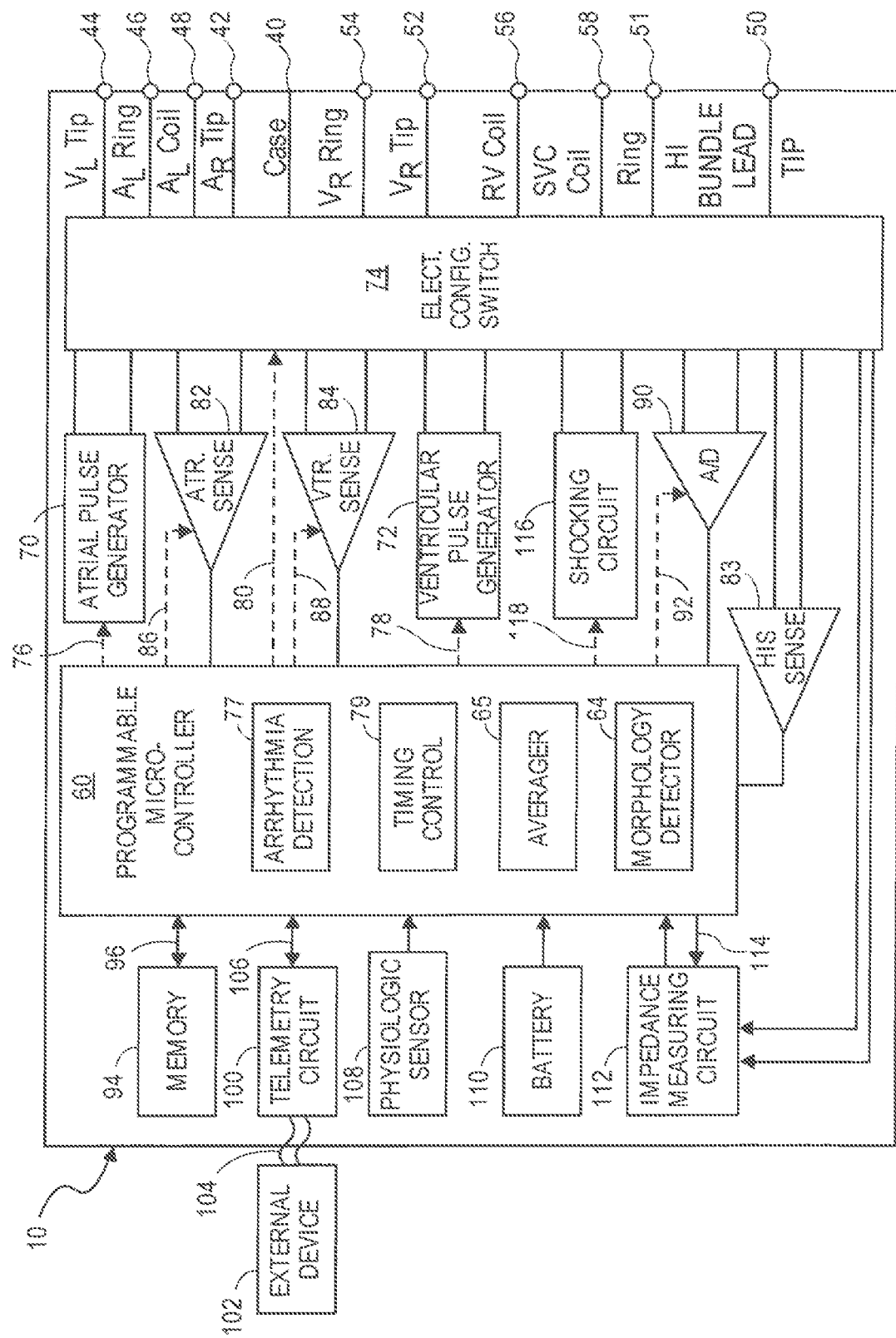
FIG. 4 is a functional block diagram of the multi-chamber implantable stimulation device of FIG. 2, illustrating the basic elements that provide pacing stimulation, cardioversion, and defibrillation in four chambers of the heart.

Referring now to FIG. 4, there is illustrated a simplified block diagram of the multi-chamber implantable stimulation device 10 of FIG. 2, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chambers) with cardioversion, defibrillation and pacing stimulation.

The housing 40 for the stimulation device 10, shown schematically in FIG. 4, is often referred to as the "can", "case" or "case electrode" and may be programmably selected to act as the return electrode for all "unipolar" modes. The housing 40 may further be used as a return electrode alone or in combination with one or more of the coil electrodes 28, 36, and 38 (shown in FIG. 2) for shocking purposes. The housing 40 further includes a connector (not shown) having a plurality of terminals 42, 44, 46, 48, 50-52, 54, 56, and 58 (shown schematically and, for convenience, next to the names of the electrodes to which they are connected). As such, to achieve right atrial sensing and pacing, the connector includes at least a right atrial tip terminal (AR TIP) 42 adapted for connection to the atrial tip electrode 22 (shown in FIG. 2).

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular tip electrode 26, the left atrial ring electrode 27, and the left atrial coil electrode 28, respectively (each shown in FIG. 2).

To support right chamber sensing, pacing and shocking, the connector further includes a right ventricular tip terminal ($V_R$ TIP) 52, a right ventricular ring terminal ($V_R$ RING) 54, a right ventricular shocking terminal (RV COIL) 56, and an SVC shocking terminal (SVC COIL) 58, which are adapted for connection to the right ventricular tip electrode 32, right ventricular ring electrode 34, the right ventricular coil electrode 36, and the SVC coil electrode 38, respectively (each shown in FIG. 2).

To achieve His bundle sensing, or sensing and stimulation, the connector further includes a His bundle lead tip terminal 50 and a His bundle lead ring terminal 51 which are adapted for connection to the His tip electrode 16 and the His ring electrode 19, respectively (each shown in FIG. 2).

At the core of the stimulation device 10 is a programmable microcontroller 60 which controls the various modes of stimulation therapy. The microcontroller 60 includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present disclosure. Rather, any suitable microcontroller 60 may be used that carries out the functions described herein.

As shown in FIG. 4, an atrial pulse generator 70 and a ventricular pulse generator 72 generate pacing stimulation pulses for delivery by the right atrial lead 20, the right ventricular lead 30, the coronary sinus lead 24, and/or the His bundle lead 21 via an electrode configuration switch 74. It is understood that in order to provide stimulation therapy in each of the four chambers of the heart, the atrial and ventricular pulse generators 70, 72 may include dedicated, independent pulse generators, multiplexed pulse generators, or shared pulse generators. The pulse generators 70, 72 are controlled by the microcontroller 60 via appropriate control signals 76, 78, respectively, to trigger or inhibit the stimulation pulses. As used herein, the shape of the stimulation pulses is not limited to an exact square or rectangular shape, but may assume any one of a plurality of shapes which is adequate for the delivery of an energy pulse, packet, or stimulus.

The microcontroller 60 further includes timing control circuitry 79 which is used to control the timing of such stimulation pulses (e.g., pacing rate) as well as to keep track of the timing of refractory periods, blanking intervals, noise detection windows, evoked response windows, alert intervals, marker channel timing, etc., which is well known in the art.

According to one embodiment of the present disclosure, timing control circuitry 79 also controls the onset and duration of a His signal sensing window during which a depolarization signal conducted through the AV node to the His bundle can be detected. Timing control circuitry 79 also controls a timing delay provided after a detected His signal detection, prior to the delivery of a right and/or left ventricular stimulation pulse.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, cross-chamber, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits 82, 84 may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

According to one embodiment of the present disclosure, a His sensing circuit 83 is selectively coupled to the His bundle lead 21 (shown in FIG. 2) for detecting the presence of a conducted depolarization arising in the atria and conducted to the His bundle via the AV node. As used herein, each of the atrial sensing circuit 82, the ventricular sensing circuit 84, and the His sensing circuit 83, includes a discriminator, which is a circuit that senses and can indicate or discriminate the origin of a cardiac signal in each of the cardiac chambers.

Each sensing circuit 82-84 preferably employs one or more low power, precision amplifiers with programmable gain and/or automatic gain control, bandpass filtering, and a threshold detection circuit to selectively sense the cardiac signal of interest. The automatic gain control enables the device 10 to deal effectively with the difficult problem of sensing the low amplitude signal characteristics of atrial or ventricular fibrillation.

The outputs of the sensing circuits 82-84 are connected to the microcontroller 60 which, in turn, is able to trigger or inhibit the atrial and ventricular pulse generators 70, 72, respectively, in a demand fashion in response to the absence or presence of cardiac activity in the appropriate chambers of the heart.

The atrial and ventricular sensing circuits 82, 84, in turn, receive control signals ever signal lines 86, 88, from the microcontroller 60 for purposes of controlling the gain, threshold, polarization charge removal circuitry (not shown), and the timing of any blocking circuitry (not shown) coupled to the inputs of the sensing circuits 82, 84.

For arrhythmia detection, the stimulation device 10 includes an arrhythmia detector 77 that utilizes the atrial and ventricular sensing circuits 82, 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation) are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90 represented by an A/D converter. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the His bundle lead 21, the coronary sinus lead 24, and the right ventricular lead 30 through the switch 74 to sample cardiac signals across any pair of desired electrodes.

In one embodiment, the data acquisition system 90 is coupled to microcontroller 60, or to other detection circuitry, for detecting a desired feature of the His bundle signal. In one embodiment, an averager 65 is used to determine a sliding average of the His bundle signal during a His signal sensing window using known or available signal averaging techniques.

Advantageously, the data acquisition system 90 may be coupled to the microcontroller 60, or other detection circuitry, for detecting an evoked response from the heart 12 in response to an applied stimulus, thereby aiding in the detection of capture. The microcontroller 60 detects a depolarization signal during a window following a stimulation pulse, the presence of which indicates that capture has occurred. The microcontroller 60 enables capture detection by triggering the ventricular pulse generator 72 to generate a stimulation pulse, starting a capture detection window using the timing control circuitry 79 within the microcontroller 60, and enabling the data acquisition system 90 via control signal 92 to sample the cardiac signal that falls in the capture detection window and, based on the amplitude, determines if capture has occurred.

Capture detection may occur on a beat-by-beat basis or on a sampled basis. Preferably, a capture threshold search is performed at least once a day during at least the acute phase (e.g., the first 30 days following device implant) and less frequently thereafter. A capture threshold search would begin at a desired starting point (either a high energy level or the level at which capture is currently occurring) and decrease the energy level until capture is lost. The minimum energy at which capture is consistently obtained is known as the capture threshold. Thereafter, a safety margin can be automatically or programmably added to the capture threshold.

Capture detection and threshold testing may also be performed for purposes of His bundle pacing. The process of performing capture threshold testing for His bundle pacing and configuring the stimulation device 10 based on the results of such testing are described in more detail below in the context of FIGS. 8A, 8B, and 9.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patients heart 12 within each respective tier of therapy.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller 60 by a control signal 106. The telemetry circuit 100 advantageously allows intracardiac electrograms and status information relating to the operation of the device 10 (as contained in the microcontroller 60 or memory 94) to be sent to the external device 102 through an established communication link 104.

In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, stimulation delays, etc.) at which the atrial and ventricular pulse generators 70, 72 generate stimulation pulses.

A common type of rate responsive sensor is an activity sensor, such as an accelerometer or a piezoelectric crystal, which is mounted within the housing 40 of the stimulation device 10. Other types of physiologic sensors are also known, for example, sensors which sense the oxygen content of blood, respiration rate and/or minute ventilation, pH of blood, ventricular gradient, etc. However, any suitable sensor may be used which is capable of sensing a physiological parameter which corresponds to the exercise state of the patient. The type of sensor used is not critical to the present disclosure and is shown only for completeness.

The stimulation device 10 additionally includes a battery 110 which provides operating power to all of the circuits shown in FIG. 4. For the stimulation device 10, which employs shocking therapy, the battery 110 must be capable of operating at low current drains for long periods of time, and then be capable of providing high-current pulses (for capacitor charging) when the patient requires a shock pulse. The battery 110 must also have a predictable discharge characteristic so that elective replacement time can be detected. Accordingly, the device 10 preferably employs lithium/silver vanadium oxide batteries, as is true for most (if not all) current devices.

The device 10 is shown in FIG. 4 as having an impedance measuring circuit 112 which is enabled by the microcontroller 60 via a control signal 114. The known uses for an impedance measuring circuit 112 include, but are not limited to, lead impedance surveillance during the acute and chronic phases for detecting proper lead positioning or dislodgement; detecting operable electrodes and conductors; and automatically switching to an operable pair if dislodgement or electrical disruption occurs; measuring respiration or minute ventilation; measuring thoracic impedance for determining shock thresholds; detecting when the device has been implanted; measuring stroke volume; and detecting the opening of heart valves, etc. The impedance measuring circuit 112 is advantageously coupled to the switch 74 so that any desired electrode may be used.

According to one embodiment of the present disclosure, the His tip electrode 16 and His ring electrode 19 may be selectively coupled via switch 74 to the impedance measuring circuit 112 for performing a tissue impedance measurement. The tissue impedance measurement may be made to determine the location of the His bundle as the His tip electrode 16 or mapping collar 418 as shown in FIG. 5, or sensing electrodes 520-523 (shown in FIG. 6) are advanced along the endocardial surface of the right atrium. A method for performing this tissue impedance measurement using the His bundle lead 21 will be described further in conjunction with FIG. 7.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (for example, up to 0.5 joules), moderate (for example, 0.5-10 joules), or high energy (for example, 11-40 joules), as controlled by the microcontroller 60. Such shocking pulses are applied to the patient's heart 12 through at least two shocking electrodes, and as shown in this embodiment, selected from the left atrial coil electrode 28, the right ventricular coil electrode 36, and the SVC coil electrode 38. As noted above, the housing 40 may act as an active electrode in combination with the right ventricular electrode 36, or as part of a split electrical vector using the SVC coil electrode 38 or the left atrial coil electrode 28 (i.e., using the right ventricular electrode 36 as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Figure 5:
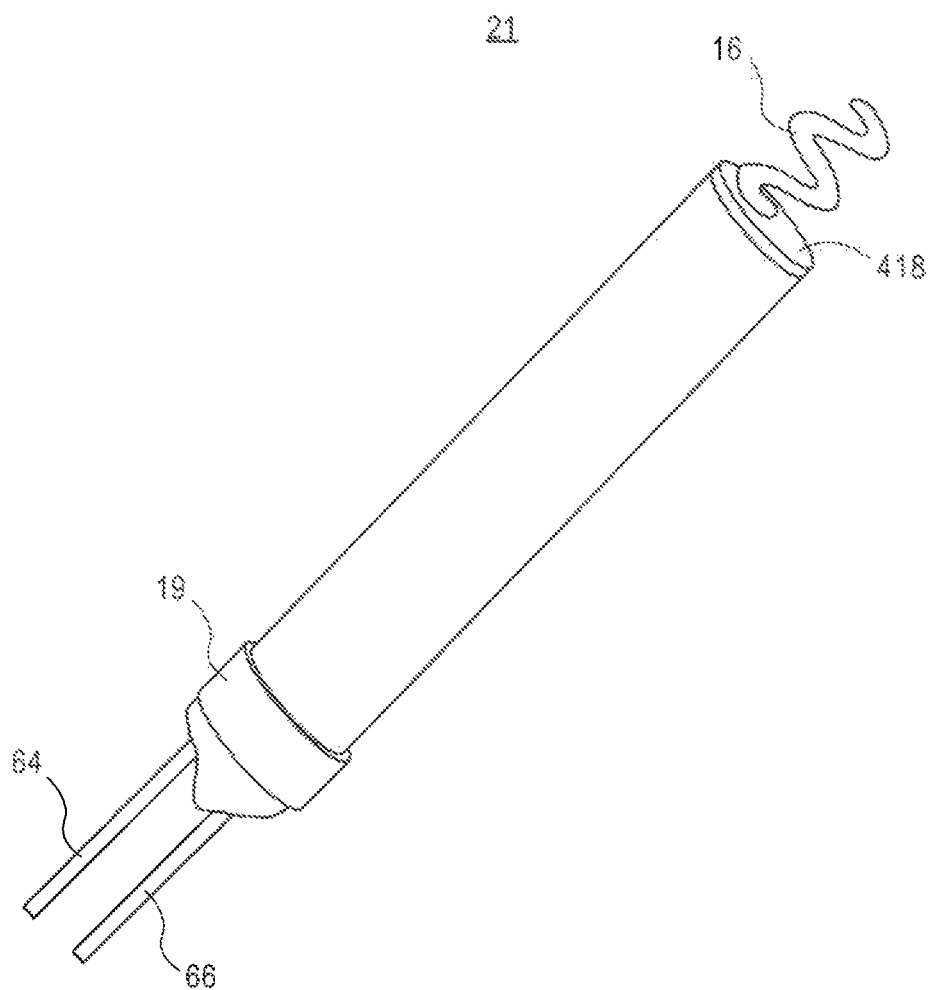
FIG. 5 is a partly fragmentary illustration of the distal end of the His bundle lead for use with the stimulation device of FIG. 4, depicting a tip electrode with an active fixation device and a non-traumatic conductive surface, and a ring electrode.

A more detailed illustration of the His bundle lead 21 is shown in FIG. 5. At the distal end of the lead 21 is the His bundle tip electrode 16. The His bundle tip electrode 16 is, or includes, an active fixation device, such as a helical, "screw-in," device that allows stable fixation of the electrode in the His bundle tissue.

The distal end of the His bundle lead 21 is further provided with a non-traumatic conductive surface (also referred to herein interchangeably as a mapping collar) 418. The non-traumatic conductive surface 418 is advantageously used to make electrical measurements that indicate the location of the His bundle without having to anchor the His bundle tip electrode 16 into the endocardial tissue. The non-traumatic conductive surface 418 and the His bundle tip electrode 16 are electrically coupled within the lead body of the His bundle lead 21 and together form one conductive element for the purposes of sensing, stimulation, and impedance measurements. Drugs, for example an acute antiarrhythmic drug such as lidocaine and/or an anti-inflammatory agent such as dexamethazone sodium phosphate, can be stored, for example, within a reservoir (not shown) at the base of the His bundle tip electrode 16 for local dispensation.

The His bundle lead 21 is also provided with a His ring electrode 19. The His ring electrode 19 is preferably spaced between approximately 2 mm and 30 mm, but preferably 10 mm, from the His tip electrode 16. The His ring electrode 19 may function as the return electrode during bipolar sensing, stimulation or impedance measurement operations.

The His tip electrode 16 and the His ring electrode 19 are each connected to flexible conductors 64, 66, respectively, which may run the entire length of the His bundle lead 21.

The flexible conductor 64 is connected to the His tip electrode 16 and is electrically insulated from the flexible conductor 66 by a layer of insulation. The conductor 66 is connected to the His ring electrode 19. The flexible conductors 64, 66 serve to electrically couple the His ring electrode 19 and the His tip electrode 16 to the His ring electrode terminal 51 and the His tip electrode terminal 50, respectively. One embodiment of the His bundle lead 21 is available from St. Jude Medical CRMD as lead model No. 1488T.

Figure 6:
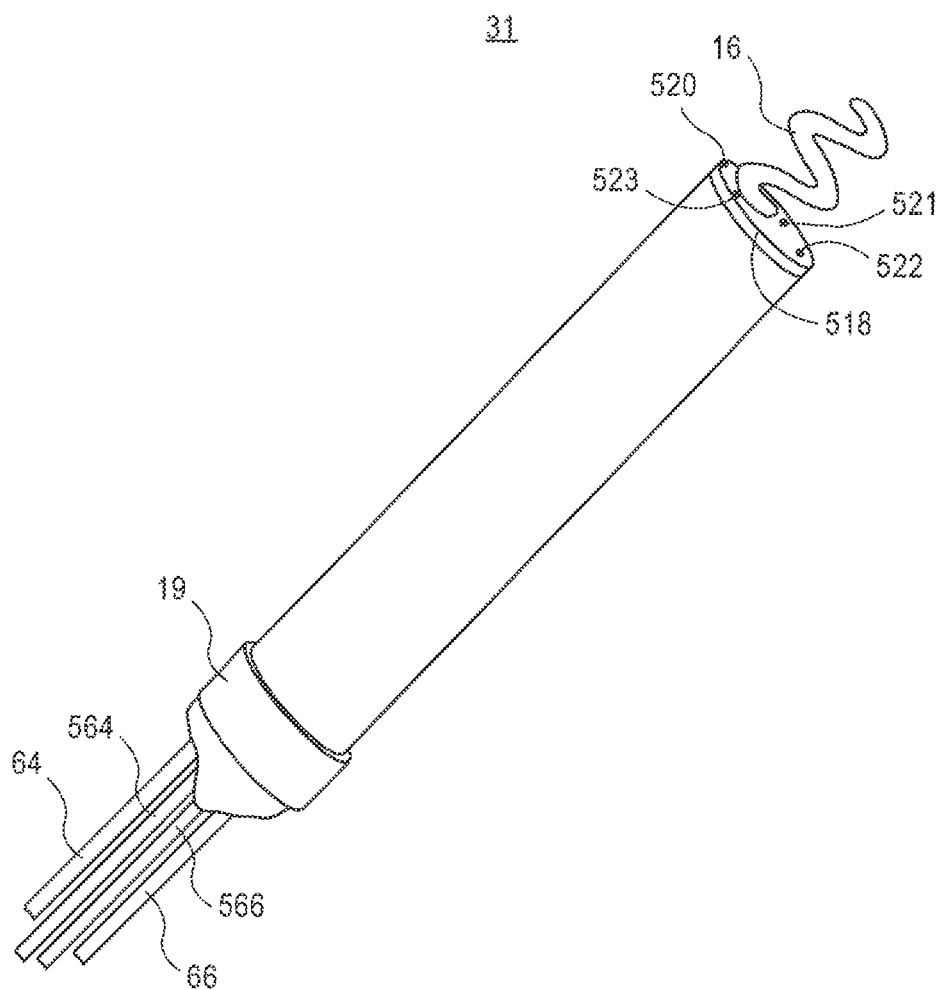
FIG. 6 is a partly fragmentary illustration of the distal end of another His bundle lead for use with the stimulation device of FIG. 4, depicting a tip electrode with an active fixation device and a non-traumatic conductive surface, a ring electrode, and four conductive sensing electrodes.

FIG. 6 illustrates an alternative His lead 31 that is generally similar in function and design to the His lead 21 shown in FIG. 5. The His lead 31 is provided with a His tip electrode 16 that includes multiple, round, closely-spaced conductive surfaces 520-523 that are arranged on a distal face 518 of the lead 31, directly facing the His bundle tissue. Though four round conductive surfaces 520-523 are shown as being uniformly distributed around the His tip electrode 16 and are electrically separated from each other by insulating material, it should be clear that a different number of conductive surfaces may alternatively be selected.

In one embodiment, a conductive surface, e.g. 520 is connected to a flexible conductor, e.g. 564 that extends along the length of the His bundle lead 31. The remaining conductive surfaces 521-523 are electrically connected together and are also connected to a flexible conductor 566 that extends along the length of the His bundle lead 31. The flexible conductors, e.g. 564, 566 are insulated from each other.

In the embodiment of FIG. 6 and with reference to FIG. 4, the device 10 includes two separate connection terminals, one for each of the two flexible conductors 564, 566 that are further connected to switch 74. The two flexible conductors 564, 566 can then be selectively connected as desired to the His sensing circuit 83, ventricular pulse generator 72, or impedance measuring circuit 112 for sensing, stimulating, and measuring tissue impedance at the site of the His bundle.

Using the lead 31, if is possible to effect stimulation with the His tip electrode 16 and the His ring electrode 19, and to effect sensing with the conductive surfaces 520-523. According to another design, the sensing is effected by the conductive surfaces 520-523 and stimulation is effected by means of the leads other than the His lead 31, for example the right atrial lead 20. For more details regarding a heart electrode equipped with multiple conductive surfaces, reference is made to U.S. Pat. Nos. 5,306,292 and 5,645,580, which are incorporated herein by reference.

During the implantation procedure, the His bundle lead 21 of FIG. 5 (or the His bundle lead 31 of FIG. 6) is introduced transvenously into the right atrium. It is then gradually advanced with the His tip electrode 16 in contact with the endocardial tissue. Electrical measurements may be made continuously as the His tip electrode 16 is advanced to determine the location of the His bundle. The non-traumatic conductive surface 418 advantageously provides electrical contact with the endocardial tissue thereby allowing electrical measurements to be performed without having to fix the His tip electrode 16 into the endocardial tissue using the His bundle tip electrode 16.

Figure 7:
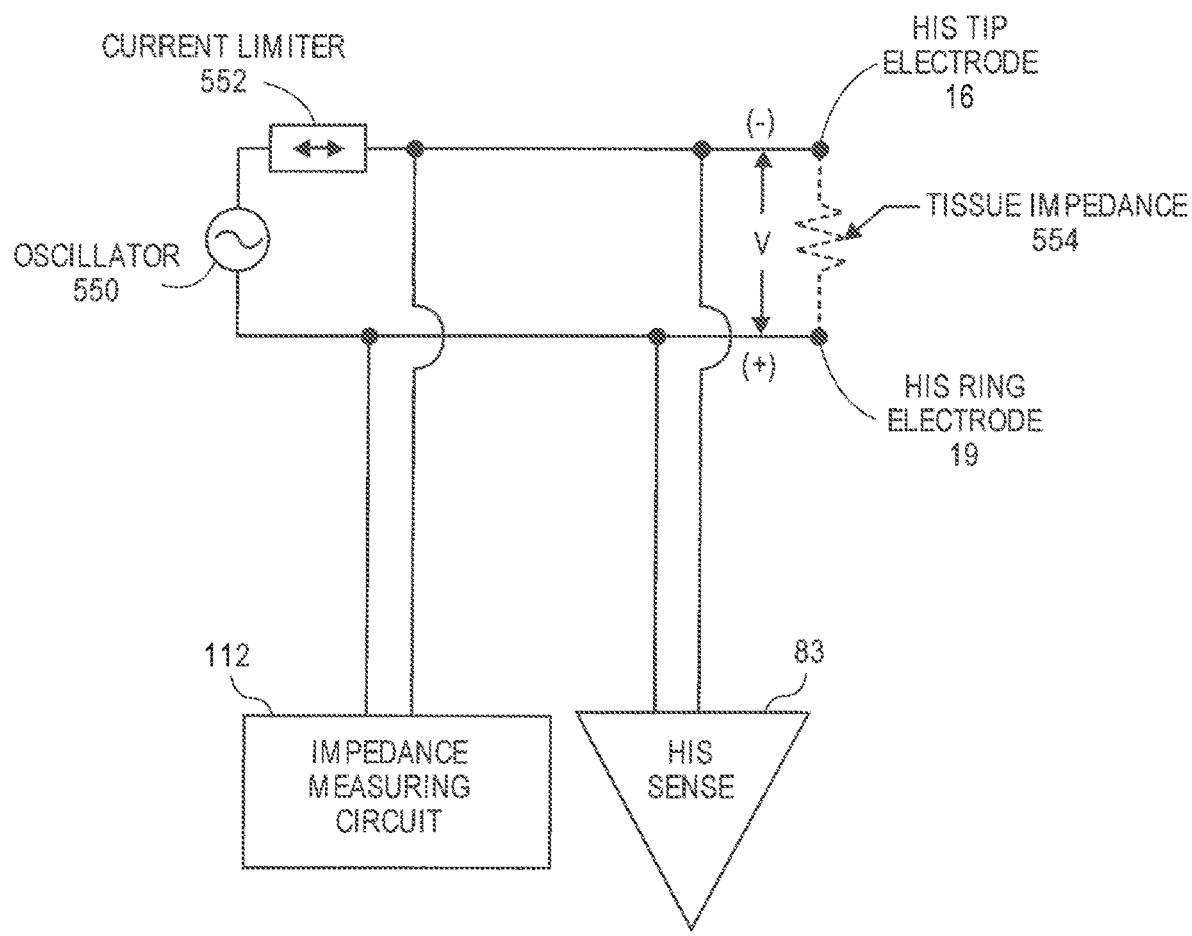
FIG. 7 is an equivalent circuit diagram illustrating a tissue impedance measurement method using the lead of FIG. 5 and the stimulation device of FIG. 4 for locating the His Bundle.

In one embodiment, tissue impedance measurements are made in order to locate the His bundle. The equivalent circuit diagram depicted in FIG. 7 represents a model by which a tissue impedance measurement can be made using the His bundle lead 21 of FIG. 5. An excitation current is applied through the His tip electrode 16. The excitation current is preferably provided as a current limited high-frequency alternating current signal produced by a 30 kHz oscillator 550 passing through a current limiter 552. A voltage signal can then be measured between the His tip electrode 16 (or the non-traumatic conductive surface 418) and the His ring electrode 19 in a bipolar fashion. The voltage signal is related to the supplied current and the tissue impedance 554 associated with the tissue in contact with the His tip electrode 16. Thus, the measured voltage signal is processed by the impedance measuring circuit 112 to determine the impedance of the tissue in contact with His tip electrode 16. The impedance equals the voltage divided by the current.

Right atrial tissue impedance is expected to be approximately twice that of the His bundle. Using the foregoing measurement method, the right atrial tissue impedance is typically on the order of 1200-1500 ohms, whereas the His bundle tissue impedance is typically on the order of 600-800 ohms. Other impedance values can be obtained using different measurement techniques. Thus, as the His bundle lead 21 is advanced in the right atrium, a large decrease in measured tissue impedance 554, of approximately 50%, indicates that the His bundle tip electrode 16 is proximate the His bundle.

The His tip electrode 16 may then be secured in the His bundle thereby anchoring the His tip electrode 16 in contact with the His bundle tissue. The electrogram signal arising from the His bundle can then be received by the His sensing circuit 83. A bypass filter (not shown) that allows signals ranging from 30-200 Hz to be received may be used to block the high frequency alternating current excitation signal produced by the oscillator 550.

Stimulation devices in accordance with this disclosure may be configured to perform a capture threshold test to classify electrical impulses generated by the stimulation device based on characteristics of the response elicited by applying the electrical impulses to a patients heart. Based on the classification, the stimulation device may then initiate and/or adjust its settings to provide optimal HBP.

Figure 8B:
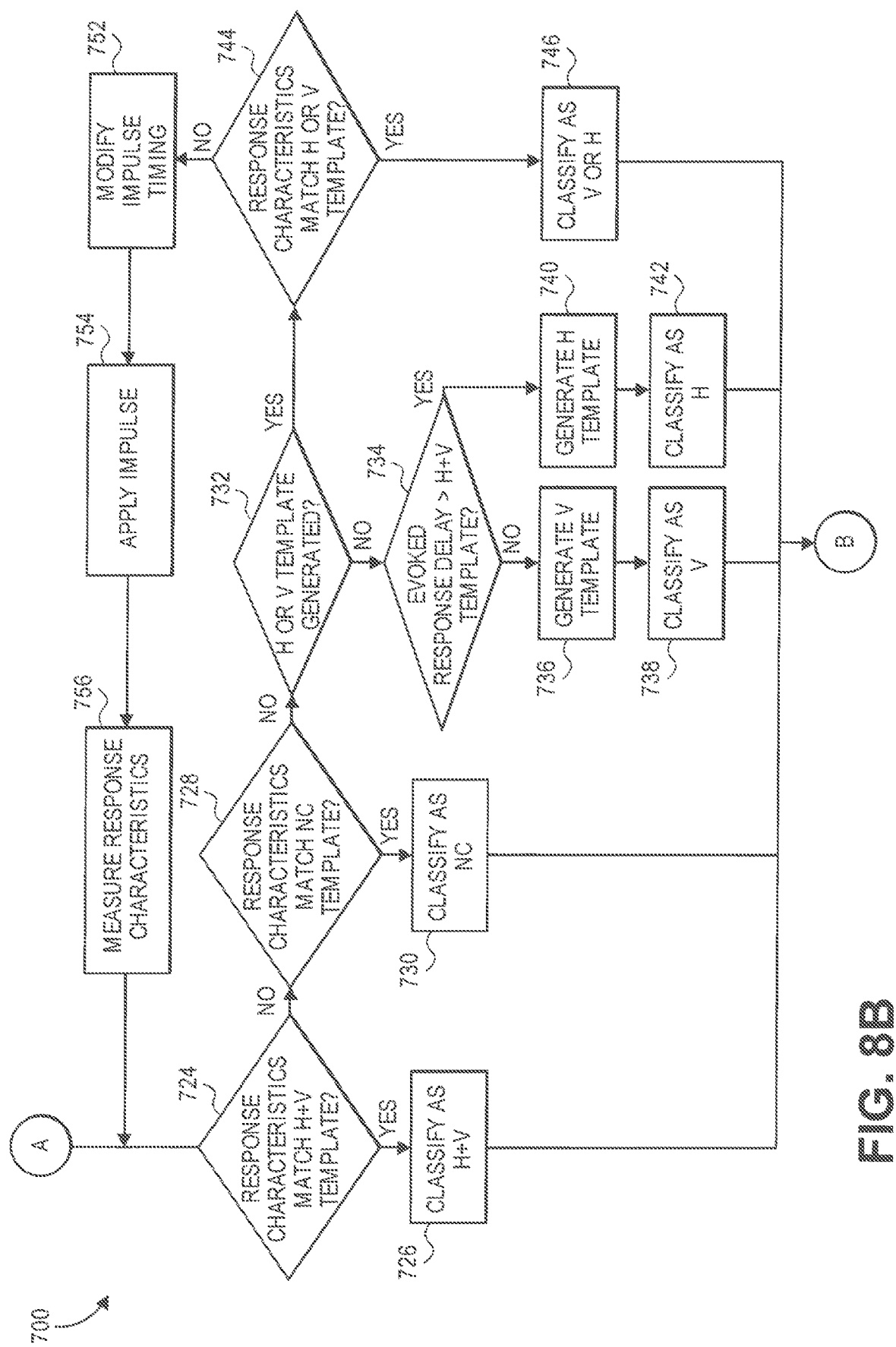

FIGS. 8A-8B include a flow chart illustrating a method 700 for conducting a capture threshold test using a stimulation device, such as the stimulation device 10 of FIG. 4. The capture threshold test comprises applying a series of electrical impulses to the His bundle via a His tip electrode, such as the His tip electrode 16, and classifying the electrical impulses based on characteristics of the response of the heart tissue to the electrical impulse. Such response characteristics may be analyzed to determine if the applied electrical impulse resulted in capture of one or more of the His bundle and the right ventricle. In certain implementations, the capture threshold test illustrated in FIGS. 8A-8B may be conducted manually by a physician, technician, or similar medical personnel that issues commands to the stimulation device 10, for example through the telemetry circuit 100 (shown in FIG. 4). In other embodiments, the capture threshold test may be implemented as a series of instructions stored within the memory 94 of the stimulation device 10 and executable by the programmable micro-controller 60 (also shown in FIG. 4).

Manual and automatic capture threshold testing may be performed at various times. For example, either of manual and automatic capture threshold testing in accordance with FIGS. 8A-8B may be performed as part of one or more of implantation, implantation follow-up, and troubleshooting of the stimulation device 10. Automatic capture threshold testing may also be performed by the stimulation device 10 according to a predetermined schedule. For example, in certain implementations, automatic capture threshold testing may be performed by the stimulation device 10 at a regular frequency during times when the patient is asleep or otherwise inactive, such as on a daily basis during the late evening or early morning. The stimulation device 10 may also initiate automatic capture threshold testing in response to detecting specific events. For example, during regular operation, the stimulation device 10 may measure response characteristics of impulses delivered by the stimulation device 10 to determine whether the current settings result in His bundle capture. If not, the stimulation device 10 may initiate or schedule an automatic capture threshold test.

As discussed below in more detail below, the method 700 generally includes applying an impulse having a predetermined voltage and duration using the stimulation device 10, measuring response characteristics of the heart, and determining whether the response characteristics indicate capture of one, both, or neither of the His bundle and right ventricle. The response characteristics may include, without limitation, the time between application of the impulse and initiation of a corresponding QRS complex (referred to herein as the "evoked response delay") and the duration of the induced QRS complex. In certain implementations, the stimulation device 10 may generate and store one or more templates including values or ranges of values for response characteristics that are indicative of particular cardiac tissue being captured. For example, the stimulation device 10 may store templates corresponding to one or more of non-selective HBP (an "H+V" template), selective HBP (an "H" template), capture of the right ventricle only (a "V" template), and non-capture of either the His bundle or right ventricle (an "NC" template).

Performing capture threshold testing generally includes each of sensing and pacing of heart tissues. For the purposes of the method 700, sensing includes sensing electrical activity of each of the His bundle and the right ventricle. Such sensing may be accomplished using various electrode configurations and sensing vectors. Referring to FIG. 2, sensing vectors that may be used to measure electrical responses for the purposes of capture threshold testing may include, without limitation, those extending between the following pairs of electrodes: (i) the atrial tip electrode 22 and the stimulation device 10; (ii) the right atrial ring electrode 23 and the stimulation device 10; (iii) the right atrial tip electrode 22 and the right atrial ring electrode 23; (iv) the right ventricle coil electrode 36 and the stimulation device 10; (v) the SVC electrode 38 and the stimulation device 10; and (vi) the right ventricle coil electrode 36 and the SVC electrode 38. In implementations in which a left ventricular lead is present, additional possible sensing vectors include those extending between: (i) the right ventricle coil electrode 36 and a coil electrode of the left ventricular lead; (ii) the SVC coil electrode 38 and the left ventricle coil electrode; and (iii) the right ventricular tip electrode 32 and a ventricular tip electrode of the left ventricular lead. Similarly, application of pacing impulses to the His bundle may be accomplished in various ways depending on the particular configuration of the pacemaker or defibrillation device. For example, His bundle pacing may be achieved along a vector defined between any of the following pairs of electrodes: (i) the His tip electrode 16 and the stimulation device 10; (ii) the His ring electrode 19 and the stimulation device 10; and (iii) the His tip electrode 16 and the His ring electrode 19.

Referring now to FIG. 8A, the method 700 includes first generating each of an H+V template and an NC template, corresponding to non-selective His bundle capture and non-capture, respectively. Generation of the H+V template may include applying a high energy impulse predetermined to induce non-selective His bundle capture (operation 702), measuring characteristics of the corresponding response (operation 704), and generating and storing an H+V template based on the measured response characteristics (operation 706). As previously noted, the H+V template may include values or ranges of values corresponding to each of an evoked response delay and a QRS complex duration.

A similar series of steps may also be performed to generate the NC template. More specifically, a low energy impulse predetermined not to induce capture of either the His bundle or right ventricle may be applied (operation 708) and the resulting response characteristics may be measured (operation 710). A back-up impulse may then be applied (operation 712). The back-up impulse is generally of a sufficient voltage and duration to capture at least the right ventricle, thereby facilitating beating of the heart despite the lack of capture during application of the low energy impulse. After the back-up impulse is applied, the NC template may be generated and stored (operation 714).

FIG. 8A illustrates generation of each of the H+V and NC templates based on a single set of response characteristics obtained after a respective impulse is applied by the stimulation device 10. In other implementations, the H+V and NC templates may be generated by collecting multiple sets of response characteristics following multiple applications of high and/or low energy impulses, respectively. The collected sets of response characteristics may then be combined to generate each of the H+V and NC templates. Accordingly, the values or ranges of values for particular response characteristics stored within the H+V and NC templates may be based on one or more measurements and may include, without limitation, averages, ranges, and similar statistical values derived from multiple response characteristic measurements.

Following generation and storage of the H+V and NC templates, the stimulation device 10 applies impulses having different stimulation voltages. The resulting responses for each impulse are then measured, analyzed, and classified based on the cardiac tissue captured as a result of each impulse. For example, in the implementation illustrated in FIG. 8A, initial impulse stimulation voltage ($V_{STIM}$) and impulse timing are each set (operations 716, 717).

The initial $V_{STIM}$ is generally set to a high starting voltage from which classification is to begin. In certain implementations, the initial voltage value may be, without limitation, one of the maximum output voltage of the stimulation device 10, the voltage previously used to generate the H+V template in operations 702-706, and a voltage that is a predetermined step below the voltage used to generate the H+V template.

The initial impulse timing may vary based on the configuration and mode of the pacemaker or defibrillator device used. For example, in the presence of an atrial lead and ventricular tracking (e.g., "DDD" pacing), the His capture threshold test may be run with an AV delay short enough to prevent competition with intrinsic conduction. This can be achieved, for example, by first lengthening the atrial sensing-to-ventricular pacing delay (for example, to 200 ms) to determine the intrinsic conduction duration. If there is an inhibition of ventricular pacing then the atrial sensing-to-ventricular pacing delay may be shortened (for example to 100 ms) and tested again. If ventricular sensing occurs, then the atrial sensing-to-ventricular pacing delay may be further shortened, for example, to 50 ms. A similar procedure can be followed for DDD devices in which atrial pacing is implemented.

If the implemented device does not include atrial lead or is otherwise programmed to operate in a single chamber mode, such as a "VVI" mode, the capture test should generally be performed at a rate that is faster than the underlying heart rate. This may be done by setting the base rate to a programmed base rate plus a predetermined rate increase (e.g., 10 ppm) for a predetermined time period (e.g., 30 seconds) and measuring the underlying rate. For example, measuring the underlying rate may be performed by calculating R-R intervals for heart beats measured during the predetermined time period. If there is no inhibition of ventricular pacing due to ventricular sensing, then the base rate may be set at the programmed base rate plus the predetermined rate increase. In alternative implementations, each of an average R-R interval and standard deviation may be determined over a predetermined time period and the base rate may be calculated based on a heart rate calculated from the R-R interval plus a factor based on the standard deviation. For example, in certain implementations, a heart rate may be calculated using the formula $HR_{AV}$=60000/R-R interval), where the R-R interval is measured in milliseconds. The ventricular pacing rate may then be set to $HR_{AV}$+3*standard deviation (ppm). In certain implementations, the process of determining the base rate may be repeated to eliminate spurious results caused by fusion.

After establishing the initial impulse timing and $V_{STIM}$ settings, the stimulation device 10 then initiates the capture test by applying an impulse (operation 718) and measuring the resulting response characteristics (operation 720).

Referring to FIG. 8B, the impulse is then classified by analyzing the response characteristics measured during operation 720. In general, the process of classifying the response characteristics includes comparing the response characteristics to values or ranges of values to determine whether the response characteristics indicate capture of one or more of the His bundle and the right ventricle. For example, in certain implementations, the response characteristics are compared to templates stored within the stimulation device 10, such as the H+V and NC templates generated during operations 706 and 714, respectively. In instances when the template includes a range of values, determining whether a particular measured response characteristic indicates capture of certain cardiac tissue generally includes determining whether the measured response characteristic fails within the range of values. In contrast, when the template includes a single value, determining whether the measure response characteristic indicates capture may include determining whether the measured response characteristic falls within a certain tolerance of the stored value. For example, a match may be considered to occur when the measured response characteristic is within one or more of an absolute tolerance, a percentage-based tolerance, and a particular number of standard deviations (if the stored value was obtained from multiple measurements).

As shown in FIG. 8B, the response characteristics may first be compared to the H+V template (operation 724) to determine whether the response characteristics correspond to non-selective capture of the His bundle (i.e., capture of both the His bundle and the right ventricle). If so, $V_{STIM}$ is classified as inducing non-selective capture ("H+V") (operation 726) and the classification is stored or otherwise recorded (operation 760), such as in a classification fable maintained in the memory 94 of the stimulation device 10.

For purposes of this disclosure, a classification table refers to a table or similar data structure maintained within the memory 94 of the stimulation device 10. The classification table includes multiple classification table entries that include a stimulation voltage and data corresponding to the stimulation voltage. The data may include, without limitation, one or more of a classification assigned during the automatic threshold capture test for the particular stimulation voltage and response characteristics generated by application of the particular stimulation voltage. Entries within the classification table may further be based on particular combinations of stimulation voltages and pulse durations such that each entry within the classification table corresponds to a unique combination of impulse voltage and duration. For ease of searching and analysis, the classification table may be organized or indexed in an ascending or descending order based on voltage/power. As described further in the context of FIG. 9, the classification table may be accessed by the microcontroller 60 of the stimulation device 10 to determine and change control output settings of the stimulation device 10.

If the response characteristics do not correspond to the H+V template, they are then compared to the NC template (operation 728). If the response characteristics correspond to those of the NC template, $V_{STIM}$ is classified as resulting in non-capture ("NC") (operation 730) and the classification results are stored in the classification table (operation 760). In certain implementations, an additional check may be performed to determine whether $V_{STIM}$ resulted in non-capture (operation 762). If capture occurred, $V_{STIM}$ may be updated (operation 764) and the process of applying an impulse using the updated $V_{STIM}$ and classifying the resulting response may be repeated. In the implementation illustrated in FIGS. 8A-8B, for example, $V_{STIM}$ is decreased by a predetermined voltage change ($\Delta V$). $\Delta V$ may be any suitable increment by which the output of the stimulation device 10 may be changed. Using a higher value for $\Delta V$ generally leads to a faster capture threshold test as fewer voltage levels of the stimulation device 10 are required to be tested. In contrast, a more granular $\Delta V$ may be used to increase the precision of the capture threshold test and, as a result, more accurately determine the voltage levels at which capture of particular cardiac tissues occur or are lost.

If application of an impulse at a particular $V_{STIM}$ results in non-capture, a back-up impulse may be applied (operation 766). Also, because any subsequent lower voltages are also likely to result in non-capture, any remaining voltage levels yet to be tested that are below $V_{STIM}$ may automatically be classified as NC within the classification table (operation 768).

Referring back to FIG. 8B, in certain instances, the response characteristics may not correspond to values representative of either of the H+V template and the NC template. In such instances, the response characteristics may be further analyzed to determine whether they indicate the occurrence of selective HBP, in which only the His bundle is captured, or ventricular pacing, in which only the right ventricle is captured. To do so, the response characteristics may be compared to values or ranges of values, which may be stored as additional templates and, more specifically, as a selective HBP ("H") template and a ventricular pacing ("V") template. Accordingly, and as illustrated in FIG. 8B, a check may be performed to determine whether either of an H template or a V template has been generated (operation 732). If so, the response characteristics may be compared to the H or V template (operation 744) and, if a match exists, the current $V_{STIM}$ may be classified accordingly (operation 746). The classification may then be stored in the classification table (operation 760).

If an H or V template does not currently exist, the response characteristics may be analyzed to determine whether they correspond to either selective HBP or to ventricular pacing and an H or V template may be generated. To do so, the QRS duration and the evoked response delay of the response characteristics may be compared to those of the H+V template. If the QRS duration is longer than that of the H+V template but the evoked response delay is approximately equal to that of the H+V template, it is likely that the current response characteristics are indicative of ventricular capture. Alternatively, if the QRS duration is approximately equal to that of the H+V template and the evoked response delay is longer, it is likely that the response characteristics correspond to selective HBP. In FIG. 8B, this process is simplified by determining whether the evoked response delay exceeds that of the H+V template (H+V). Accordingly, based on the outcome of the comparison, either a ventricular capture (V) template or a selective HBP template (H) or may be generated based on the response characteristics (operations 736, 740) and the response characteristics may be classified accordingly (operations 738, 742). The resulting classification may then be stored in the classification table (operation 760).

Due various factors, which may include the physiology of the heart and the location of stimulating electrodes, the method 700 will typically generate only one of the H and the V template. More specifically, heart physiology generally dictates one of two capture sequences as impulse energy is reduced. In the first sequence, high energy impulses result in non-selective HBP in which both of the His bundle and right ventricle are captured. As impulse energy is reduced, selective HBP occurs resulting from capture of the His bundle only. As impulse energy is further reduced, neither the His bundle or the right ventricle is captured. In the second sequence, high energy impulses similarly result in non-selective HBP. However, as impulse energy is reduced, only the right ventricle is captured and, as impulse energy is further reduced, non-capture results. As a result, if the physiology of the patient's heart conforms to the first sequence, only an H template is likely to be generated and if the physiology of the patient's heart results in the second capture sequence, a V template will be generated.

A number of scenarios may occur where the response characteristics do not match any of the generated templates. Such situations may include what are referred to herein as fusion, pseudo-fusion, and hemi-capture. Fusion occurs when conduction resulting from the impulse delivered during operation 718 coincides with the intrinsic conduction of the patient's heart. In contrast, pseudo-fusion occurs when an ineffective impulse is delivered during the absolute refractory period. In each of fusion and pseudo-fusion, the response characteristics resulting specifically from the impulse cannot be readily distinguished from the intrinsic response of the heart. Finally, hemi-capture occurs when the impulse results in capture of only one of the right bundle fibers and the left bundle fibers of the His bundle, leading to incomplete electrical communication between the His bundle and the ventricles.

To discriminate between fusion, pseudo-fusion, and hemi-capture, the timing of the impulse may be varied (operation 752). More specifically, the delay between sensing electrical activity and delivering an impulse to the His bundle is varied from the timing implemented during operation 718. For example, in implementations including each of an atrial lead and a His bundle lead, the timing between sensing electrical activity of the atrium (e.g., by observing a P wave) and applying an impulse to the His bundle may be increased or decreased by a predetermined interval. The impulse is reapplied using the new timing (operation 754) and a new set of response characteristics are measured (operation 756). The process of classifying the new response characteristics then proceeds to determine whether the new timing has resolved the inability to classify the original response characteristics. Subsequent storage of a classification table entry in the classification table (during operation 760) may further include storing the modified timing.

In certain implementations, the new response characteristics obtained using the modified timing are compared with the response characteristics originally obtained during operation 720 to provide further information and, more specifically, to identify whether the inability to classify the original impulse was the result of fusion, pseudo-fusion, or hemi-capture. If the response characteristics obtained using the modified timing are consistent with the originally obtained response characteristics, hemi-capture is likely. More specifically, if the evoked response delays and/or QRS complex morphology are consistent, it is likely that electrical impulses are unable to properly proceed through one of the left and right His bundle fibers. Similarly, comparison of the new and original response characteristics may identify the occurrence of pseudo-fusion and/or fusion. For example, if the timing between atrial sensing and His bundle pacing is increased, and the resulting response characteristics indicate consistent QRS morphology but a reduced evoked response delay, pseudo-fusion likely occurred. In contrast, if QRS morphology differs between the modified and original timing, fusion likely occurred.

Data corresponding to the identification and detection of fusion, pseudo-fusion, and hemi-capture may be stored within the memory 94 of the stimulation device 10 for later retrieval and diagnostic analysis. For example, in certain implementations, the stimulation device 10 may generate and store a log in which data corresponding to fusion, pseudo-fusion, hemi-capture, and similar events is recorded. Such data may include, without limitation, a date/time stamp, the response characteristics corresponding to the event, the stimulation device settings that resulted in the event, and the stimulation device settings that circumvented the event.

If response characteristics obtained using modified impulse timing are still unable to be classified, the impulse timing may be further modified and another set of response characteristics may be obtained and analyzed to determine whether classification is possible. In certain implementations, the number of times that the impulse timing is modified may be limited such that after the limit is exceeded, the current $V_{STIM}$ is classified as resulting in non-capture. Also, to the extent the response characteristics measured during operation 756 indicate non-capture of a portion of the heart tissue, a back-up impulse may be delivered.

Figure 9:
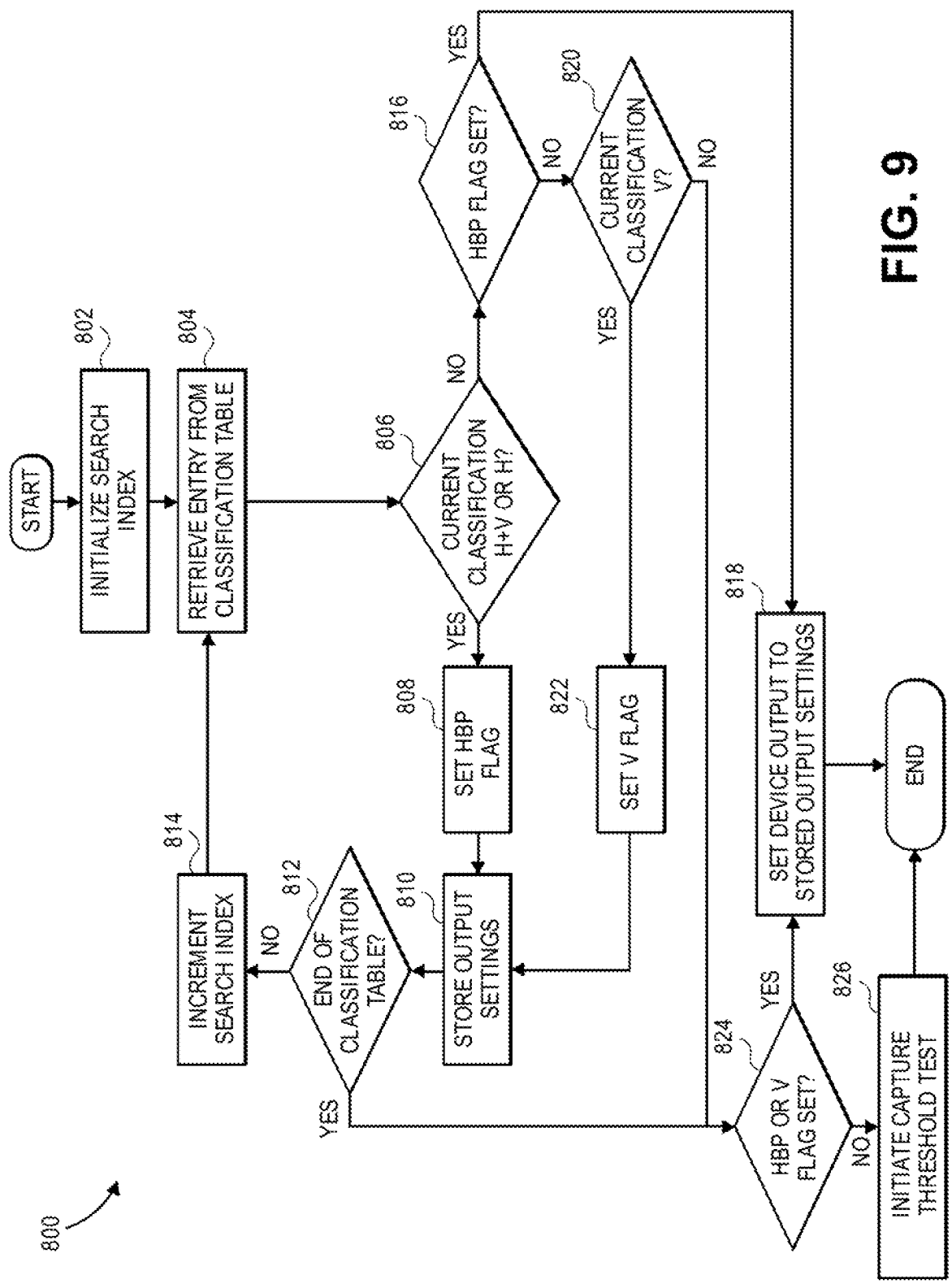
FIG. 9 is a flow chart illustrating a method for initializing a stimulation device, such as the stimulation device of FIG. 2.

FIG. 9 is a flow chart illustrating a method 800 of initializing output settings of a stimulation device, such as the stimulation device 10. In certain implementations, initialization of the stimulation device 10 includes identifying the lowest energy impulse capable of capturing the His bundle, regardless of whether capture of the His bundle is selective or non-selective. In the event that His bundle capture is not possible, initialization further includes identifying the lowest energy impulse capable of capturing the right ventricle.

During initialization, the stimulation device 10 and, more specifically, the microprocessor 60 of the stimulation device 10, determines and applies initial output settings. In certain implementations, the microprocessor 60 may search or otherwise analyze data stored in the memory 94 of the stimulation device 10 to determine the initial output settings. For example, the memory 94 may store a classification table including entries that form a list of possible output settings of the stimulation device 10 and corresponding classifications for the responses generated by applying an impulse according to the output settings. For purposes of the method 800, the output settings generally correspond to a His bundle electrode adapted to provide pacing of the His bundle, however, in configurations in which other pacing electrodes are implemented, additional output settings for pacing of other heart tissue may further be loaded by the stimulation device 10 during the initialization process.

The method 800 assumes that a classification table has been created that includes an ordered list of output settings arranged by output energy and that each entry in the classification table is associated with an index. The method 800 further assumes that the classification table is arranged or indexed such that as the search index is incremented, the classification table entries that are retrieved and analyzed correspond to progressively lower output settings. Accordingly, the method 800 includes initializing a search index (operation 802) and retrieving an entry corresponding to the index from the classification table (operation 804).

The retrieved record is then analyzed to determine whether the entry corresponds to settings that were previously classified (such as during the threshold capture test illustrated in FIGS. 8A-8B) as evoking either non-selective (H+V) or selective (H) His bundle capture (operation 806). If the output settings of the current classification table entry resulted in His bundle capture, a flag (HBP flag) is set indicating that an HBP-suitable setting has been identified (operation 808) and the output settings are stored as potential output settings of the stimulation device 10 (operation 810). If the current index does not correspond to the end of the classification table (operation 812), the search index is incremented (operation 814) and the process of retrieving and analyzing the corresponding classification table entry is repeated. To the extent subsequent classification table entries are also classified as either H or H+V, the temporarily stored settings will continue to be updated to reflect the lowest power settings for which His bundle capture was identified.

If the current classification table entry is not classified as either H or H+V, a check is performed to determine whether the HBP flag has been set (operation 816). In other words, a check is performed to determine whether output settings are currently stored that result in capture of the His bundle. If the HBP flag is set, the stored settings are applied to the stimulation device 10 (operation 818) and the initialization process ends. In certain implementations, application of the stored settings to the stimulation device 10 includes setting the output setting of the stimulation device 10 to match the stored output settings. In other implementations, the output settings of the stimulation device 10 may correspond to the stored output settings augmented by a safety factor. The safety factor may include, without limitation, one or more of a quantity added to one or more of the stored output settings or a factor by which one or more of the stored output settings are multiplied.

If, on the other hand, the HBP flag has not been set, the implication is that no output settings were identified that resulted in His bundle capture. A check is then performed on the current classification table entry to determine whether if has been classified as resulting in ventricular capture (V) (operation 820). If so, a corresponding flag (V flag) is set (operation 822), the output settings corresponding to the current classification table entry are stored (operation 810), and the search index is incremented (operation 814). To the extent any subsequent classification table entries are also classified as V, the stored output settings will be updated such that the stored output settings reflect the lowest output settings capable of ventricular capture.

When the end of the classification table is reached (as determined by operation 812) or the current classification table entry is not classified as any of H, H+V, or V (as determined by operation 820), a check is performed to determine whether either of the HBP or V flags have been set (operation 824), thereby checking whether output settings have been stored. If so, the output settings of the stimulation device 10 (operation 818) are set to the stored output settings and the initialization process ends.

If neither of the HBP or V flag have been set, then the initialization process failed to identify any settings capable of capturing either the His bundle or ventricle and remedial measures may be initiated. For example, in the method 800, a capture threshold test, such as the capture threshold test illustrated in FIGS. 8A-8B, may be initiated to generate an updated classification table. In certain implementations, capture threshold testing may also be initiated upon determining that the classification table does not include any entries classified as resulting in His bundle capture (i.e., H+V or H).

Figure 10:
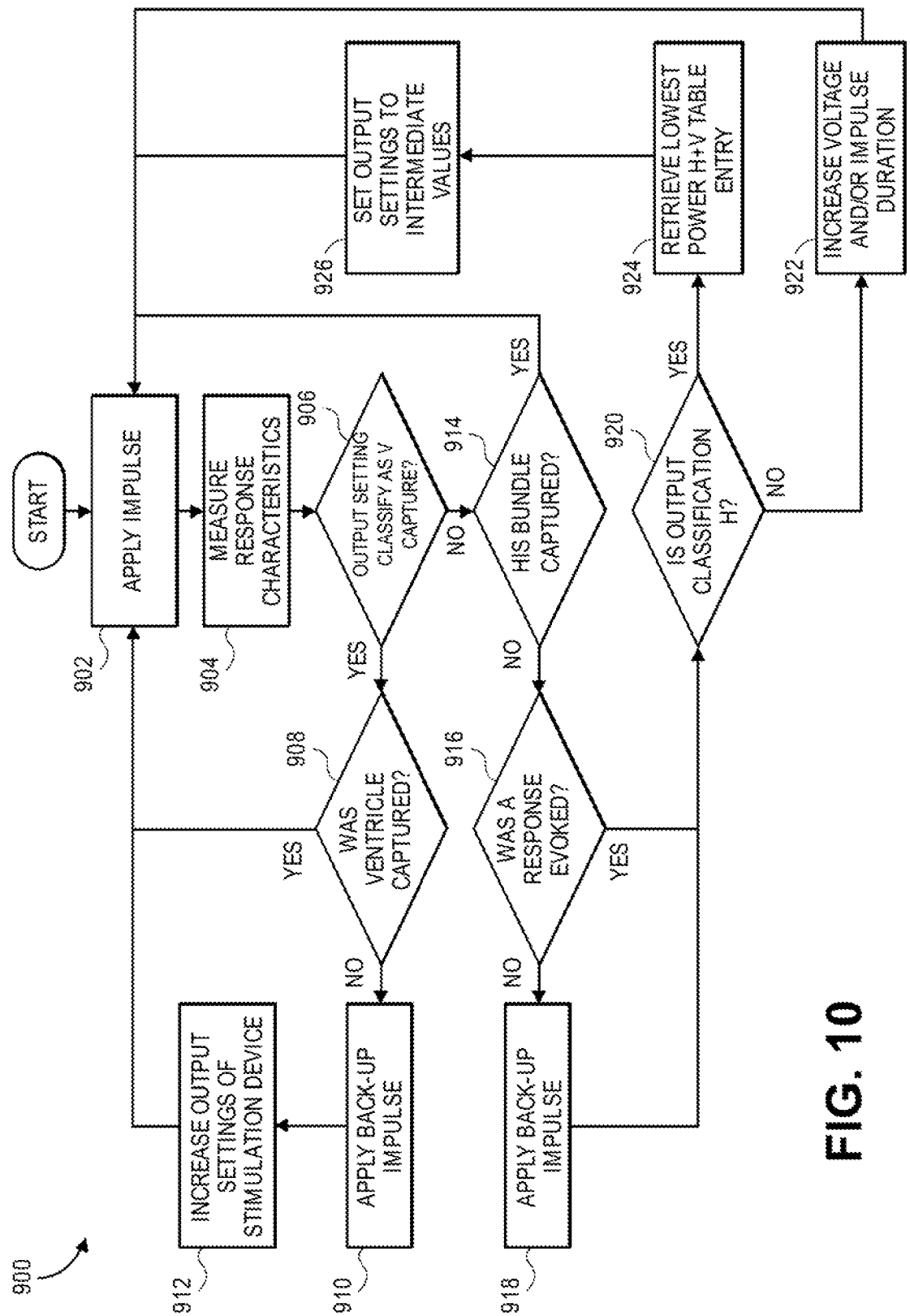
FIG. 10 is a flow chart illustrating a method for operating a stimulation device, such as the stimulation device of FIG. 2.

FIG. 10 illustrates a method 900 of operating a stimulation device 10 subsequent to the initialization process illustrated in FIG. 9. In general, operation of the stimulation device 10 includes applying an impulse based on the current output settings of the stimulation device 10, measuring response characteristics resulting from application of the impulse, and determining whether the response characteristics are consistent with the classification associated with the output settings of the stimulation device 10. To the extent the response characteristics are inconsistent with the classification, the output settings of the stimulation device 10 are modified for the subsequent impulse. The method 900 presumes that the output settings of the stimulation device 10 have been initialized. Initialization of the output settings may include executing an initialization process, such as that illustrated in FIG. 9, or may include loading previously stored output settings.

The method 900 includes applying an impulse (operation 902) according to the settings applied during initialization and measuring the corresponding response characteristics (operation 904). Following measurement of the response characteristics, a check is performed to determine whether the current output settings were previously classified as inducing ventricle-only capture (V) (operation 906). If so, a subsequent evaluation of the response characteristics is performed to determine whether the ventricle was capture (operation 908). Evaluation of the response characteristics may include comparison of the response characteristics to one or more templates including values or ranges of values indicative of ventricle-only capture. Such templates may, for example, be generated as part of a capture threshold test, such as the capture threshold test illustrated in FIGS. 8A-8B.

If the response characteristics are consistent with ventricle-only capture, the operational loop is reinitiated by applying a subsequent impulse using the existing output settings. If, on the other hand, the ventricle was not captured, a back-up impulse may be applied (operation 910) and the output settings of the stimulation device 10 may be increased (operation 912). Increasing the output settings of the stimulation device 10 may include, without limitation, increasing one or both of the output voltage and pulse duration settings of the stimulation device 10. Increasing an output setting may include, without limitation, one or more of increasing the output setting by a predetermined amount, multiplying the output setting by a predetermined factor, or modifying the output setting based on settings data stored within a classification table. In implementations in which the output settings are modified based on a classification table, such modification may include identifying the next highest output setting classified as resulting in ventricle-only capture and setting the output settings of the stimulation device 10 to the next highest output setting. Alternatively, the output settings of the stimulation device 10 may be set to an average or weighted average of the current and next highest output settings.

If the output settings of the stimulation device 10 are not classified as ventricle-only capture, a subsequent check may be performed to determine if the impulse resulted in capture of the His bundle (operation 914). If the His bundle was captured, the operational loop may be reinitiated. Alternatively, a check may be conducted to determine whether the impulse evoked a response (operation 916), such as a QRS complex, by analyzing the response characteristics. In the event the impulse did not produce a response, a back-up impulse may be applied to ensure a heartbeat (operation 918).

Whether a response was evoked by the original impulse or the back-up impulse, the original impulse is then modified in an attempt to adjust the output settings to result in His bundle capture. Generally, modifying the output settings involves increasing at least one of the output voltage and impulse duration, thereby increasing the overall energy of the impulse. As previously discussed in the context of ventricle-only capture, modification of the output settings of the stimulation device 10 may include, without limitation, one or more of increasing an output setting of the stimulation device 10 by a predetermined amount, multiplying the output setting by a predetermined factor, or modifying the output setting based on settings data stored within a classification table.

In certain implementations, the type of modification applied to the output settings may vary based on the classification assigned to the original output settings of the stimulation device 10. For example, in the method 900 a check is performed to determine whether the initial output settings were classified as resulting in selective His bundle capture (H) (operation 920). If not, the method 900 assumes the original classification corresponded to non-selective His bundle capture (H+V) and one of the voltage and impulse duration is increased by a predetermined amount (operation 922). If, on the other hand, the original output settings were classified as H, a more complex modification is undertaken. Specifically, the lowest power entry in the classification table resulting in non-selective His bundle capture is identified and retrieved (operation 924). The output settings of the stimulation device 10 are then changed to an intermediate value between the current output settings and those corresponding to the lowest power H+V table entry (operation 926).

After modification of the output of the stimulation device 10, the process of applying an impulse based on the current settings of the stimulation device 10, measuring corresponding response characteristics, and analyzing the response characteristics to determine if they are consistent with the output setting classification are repeated. In certain implementations, failure to capture the His bundle may automatically trigger initiation of a capture threshold test, such as the capture threshold test illustrated in FIGS. 8A-8B.

The methods illustrated in FIGS. 8A-10 are example methods in which sensing and stimulation are applied primarily to the His bundle and the right ventricle. In other implementations in accordance with this disclosure, other heart tissue may be sensed and stimulated instead of or in addition to the right ventricle. Such heart tissue may include, without limitation, one or more of the right atrium, the left atrium, and the left ventricle. For example and with reference to FIGS. 8A-8B, in certain implementations, the "V" template may correspond to a response of any of the left ventricle, the right atrium, and the left atrium instead of the right ventricle. Alternatively, in addition to the "V" template corresponding to a response of the right ventricle, additional templates may be generated for one or more of the left ventricle, the right atrium, and the left atrium. In either case, the templates corresponding to the left ventricle, the right atrium, and the left atrium may be used instead of or in conjunction with a template corresponding to the right ventricle for purposes of classifying impulses (for example, as illustrated in FIGS. 8A-8B) and dynamically controlling an implantable cardiac stimulating device (for example, as illustrated in FIG. 10).

Implantable cardiac stimulating devices in accordance with this disclosure may also store data related to their operation and may make such data available for retrieval and analysis. For example, and referring to the stimulation device 10 depicted in FIGS. 2 and 4, data may be collected and stored by in the memory 94 and made available to one or more external devices, such as the external device 102, using the telemetry circuit 100. In certain implementations, data made available from the stimulation device 10 may include, without limitation, any templates generated and/or stored within the stimulation device for classifying impulse responses, classification tables used to initialize settings of the stimulation device 10, and one or more logs used to record one or both of device activity and cardiac activity. Such data may be recorded over time to facilitate identifying trends that may correspond to changes in the stimulation device 10 or components thereof or the cardiac tissue to which the stimulation device 10 is coupled. For example, such trend data may include a summary diagnostic that may include a count or percentage of selective and non-selective His bundle pacing events over a period of time. As another example, such data may include measurements of the capture threshold over time, which may be used to identify improvement or degeneration of heart tissue based on whether the capture threshold is decreasing or increasing over time, respectively.

In implementations in accordance with this disclosure, the stimulation device 10 captures and analyzes electrical activity of the heart for various purposes. For example, in the method 700 of FIGS. 8A and 8B, response characteristics produced by applying an impulse to the heart are measured during various operations (for example, each of operations 704, 710, and 720). One characteristic that may be determined and used to evaluate whether His bundle capture has occurred and whether the capture is selective of non-selective is the duration of the QRS complex produced subsequent to the application of an impulse by the stimulation device 10. Accordingly, stimulation devices in accordance with this disclosure may be able to determine the duration of a QRS complex using various methods.

FIG. 11 is a flow chart describing an example method 1100 for determining QRS complex duration. Generally, the method 1100 involves identifying each of a start time and end time of the QRS complex and then determining the length of the interval between the start and end times. To do so, the method 1100 includes capturing electrical data (operation 1102), the electrical data corresponding to a cardiac response, such as a QRS complex, following application of an electrical impulse from a stimulation device. For example, the stimulation device may be configured to sample signals from sensing electrodes for a predetermined time period (e.g., 300 ms) following application of an impulse by the stimulation device and to store the sampled data. An example of such collected data is illustrated in FIG. 12A, which depicts a graph 1200 including millivolt readings overtime corresponding to a GRS complex following application of an electrical impulse to cardiac tissue.

After receiving the electrical data, the data may be processed and analyzed to determine the duration of the QRS complex. In the method 1100, for example, the absolute value of the first derivative of the electrical data is taken (operation 1104) such that an absolute rate of change of the electrical readings may be determined. The graph of FIG. 12B is a graph 1300 of the absolute first derivative of the electrical data of FIG. 12A and, as a result, depicts the absolute rate of change of the electrical activity (in millivolts (mV)/ms) over time.

The duration of the QRS complex may be determined from the absolute first derivative data in various ways. For example, in certain implementations, the maximum value of the absolute first derivative is identified (operation 1106). In the example data of FIGS. 12A and 12B, the maximum absolute first derivative is 0.17 mV/ms and occurs at approximately 90 ms and is indicated by an "X" 1302. Next, a threshold value may be calculated based on the maximum value (operation 1108). The threshold value is generally selected to distinguish between possible noise or similar transients in the electrical signal and the actual electrical response of the cardiac tissue to the impulse and, as a result, may vary from application to application. In the current example, however, the threshold value is calculated as 5% of the maximum absolute first derivative, or approximately 0.0085 mV/ms, which is indicated in the graph 1300 by a threshold line 1304.

After establishing the threshold, the start time of the QRS complex is determined (operation 1110). In the current example, the absolute first derivative values are compared to the threshold beginning at the time the impulse was applied (t=0 ms). The start time of the QRS complex is then identified as the time at which the absolute first derivative value first crosses the threshold 1304. In the example illustrated in FIG. 12B, this occurs at approximately 50 ms and is indicated by a first dashed line 1306. The end time of the QRS complex may then be determined in a similar process (operation 1112). More specifically, the absolute first derivative values are compared to the threshold beginning at the end of the sampled data (i.e., t=250 ms). The end time of the QRS complex is then identified as the time at which the absolute first derivative value of the electrical signal crosses the threshold 1304, which is indicated in the graph 1300 with a second dashed line 1308. Referring again to the example in FIG. 12B, the QRS complex end time occurs at approximately t=127 ms. The QRS duration may then be calculated (operation 1114), for example, by determining the difference between the QRS complex start time and the QRS complex end time and which in the example is approximately 77 ms. The calculated QRS complex duration may then be used to perform various evaluations and analyses as previously described herein including, but not limited to, the creation of templates and classification of impulse responses.

The foregoing merely illustrates the principles of the present disclosure. Various modifications and alterations to the described embodiments will be apparent to those skilled in the art in view of the teachings herein. It will thus be appreciated that those skilled in the art will be able to devise numerous systems, arrangements and methods which, although not explicitly shown or described herein, embody the principles of the disclosure and are thus within the spirit and scope of the present disclosure. From the above description and drawings, it will be understood by those of ordinary skill in the art that the particular embodiments shown and described are for purposes of illustrations only and are not intended to limit the scope of the present disclosure. References to details of particular embodiments are not intended to limit the scope of the disclosure.

What is claimed:

1. A method of pacing a His bundle of a patient heart using a stimulation system, the stimulation system having a memory, a pulse generator, a stimulating electrode disposed in proximity to the His bundle, and at least one sensing electrode adapted to sense electrical activity of the patient heart, the method comprising:
applying, using the pulse generator, a plurality of impulses through the stimulating electrode to induce a plurality of responses from the patient heart, the plurality of impulses having different impulse energies corresponding to a respective output setting of the stimulation system;
measuring, using the sensing electrode, response characteristics for the plurality of responses;
assigning corresponding classifications to the plurality of responses based on whether the respective response characteristics indicate capture of one or both of the His bundle and a ventricle of the patient heart, the response characteristics including an evoked response delay, the assigning based at least in part on the evoked response delay; and
for each impulse, storing each of the output setting and the classification associated with the impulse in the memory.

2. The method of claim 1, wherein the response characteristics further include a QRS complex duration, the assigning comprising assigning a classification of selective HIS bundle capture when the response characteristic has a first QRS complex and assigning a classification of non-selective HIS bundle capture when the response characteristic has a second QRS complex that is wider than the first QRS complex.

3. The method of claim 2, wherein determining the QRS complex duration comprises:
calculating first derivative data of the response characteristics; identifying each of a QRS complex start time and a QRS complex end time by comparing the first derivative data to a predetermined threshold; and
calculating the QRS complex duration as the difference between the QRS end time and the QRS start time.

4. The method of claim 1, wherein the output setting comprises at least one of a stimulation voltage and an impulse duration.

5. The method of claim 1, further comprising:
generating a plurality of templates, each template corresponding to values indicating capture of cardiac tissue; and
storing the plurality of templates in the memory,
wherein assigning an impulse a classification comprises identifying a template of the plurality of templates corresponding to the response characteristics of the impulse.

6. The method of claim 5, wherein the plurality of templates comprise templates for identifying each of selective His bundle capture, non-selective His bundle capture, ventricle-only capture, and non-capture of the His bundle and the ventricle.

7. The method of claim 5, wherein generating a template of the plurality of templates comprises:
applying a predetermined impulse selected to capture specific cardiac tissue;
measuring response characteristics of the predetermined impulse; and assigning a value or range of values to the template based on the response characteristics of the predetermined impulse.

8. The method of claim 1, wherein the memory comprises an ordered table arranged in order of impulse energy, and wherein storing each of the output settings and the classification in the memory comprises generating a record in the ordered table including the output settings and the classification.

9. The method of claim 1, further comprising configuring output settings of the stimulation system, wherein configuring output settings of the stimulation system comprises:
identifying a lowest-energy impulse of the plurality of impulses classified as resulting in capture of at least the His bundle or, if no impulse is classified as resulting in capture of the His bundle, as resulting in capture of the ventricle;
retrieving, from the memory, the output settings associated with the lowest-energy impulse; and
setting the output setting of the stimulation system based on the output settings associated with the lowest-energy impulse.

10. The method of claim 9, wherein setting the output setting of the stimulation system comprises setting the output setting of the stimulation system to the output settings associated with the lowest-energy impulse augmented by a safety factor.

11. The method of claim 1, further comprising, for each impulse classified as indicating non-capture of the His bundle and the ventricle, applying a back-up impulse, the back-up impulse having an energy sufficient to capture at least one of the His bundle and the ventricle.

12. The method of claim 1, wherein the assigning further comprises assigning a classification of selective HIS bundle capture when the response characteristic has a first evoked response delay and assigning a classification of non-selective HIS bundle capture when the response characteristic has a second evoked response delay that is shorter than the first evoked response delay.

13. The method of claim 12, wherein the selective His bundle capture indicates that only the His bundle was captured by the corresponding one of the plurality of impulses and the myocardium was not excited, wherein the non-selective HIS bundle capture indicates that the corresponding one of the stimulus results in simultaneous capture of both the His bundle and the myocardium.

14. A cardiac stimulation system, the system comprising:
a stimulation electrode;
one or more sensing electrodes;
a pulse generator adapted to generate electrical impulses for pacing the His bundle;
a processor communicatively coupled to the pulse generator and adapted to receive response characteristics from the one or more sensing electrodes; and
a memory communicatively coupled to the processor, the memory including instructions executable by the processor that, when executed by the processor, cause the processor to:

generate, using the pulse generator, a plurality of impulses to induce a plurality of responses from the patient heart, the plurality of impulses corresponding to different output settings of the pulse generator;

receive, from the sensing electrode, response characteristics for the plurality of responses;

assign corresponding classifications to the plurality of responses based on whether the respective response characteristics indicate capture of one or both of the His bundle and the ventricle, the response characteristics including an evoked response delay, the classification assigned at least in part based on the evoked response delay; and for each impulse, store the output setting and the classification associated with the impulse in the memory.

15. The cardiac stimulation system of claim 14, wherein the instructions further cause the processor to:

identify, from the memory, a lowest-energy impulse of the plurality of impulses classified as resulting in capture of at least the His bundle or, if no impulse is classified as resulting in capture of the His bundle, as resulting in capture of the ventricle; and set an output setting of the pulse generator based on the output settings associated with the lowest-energy impulse.

16. The cardiac stimulation system of claim 15, wherein identifying the lowest-energy impulse comprises accessing a table stored in the memory, the table including a plurality of entries, each entry including a respective output setting and a respective classification.

17. The cardiac stimulation system of claim 15, wherein the instructions further cause the processor to:

apply, using the pulse generator, a pacing impulse to the patient heart using the output settings;

receive, from the one or more sensing electrodes, response characteristics corresponding to the pacing impulse;

determine that the pacing impulse response characteristics indicate at least one of capture or non-capture of heart tissue and are inconsistent with the classification of the lowest-energy output setting; and modify the output settings of the stimulation device to have an increased energy.

18. The cardiac stimulation system of claim 14, wherein the response characteristics include each of a QRS complex duration and an evoked response delay.

19. The cardiac stimulation system of claim 14, further comprising:

the stimulation electrode electrically coupled to the pulse generator by a stimulation electrode lead and adapted to deliver impulses generated by the pulse generator to the patient heart; and the one or more sensing electrodes electrically coupled to the processor by a sensing electrode lead and adapted to sense response characteristics of the His bundle and the ventricle in response to impulses delivered by at least one stimulation electrode.

20. The system of claim 14, wherein the processor is configured to assign a classification of selective HIS bundle capture when the response characteristic has a first evoked response delay and to assign a classification of non-selective HIS bundle capture when the response characteristic has a second evoked response delay that is shorter than the first evoked response delay.

21. The system of claim 20, wherein the processor is configured to assign the selective His bundle capture to indicate that only the His bundle was captured by the corresponding one of the plurality of impulses and the myocardium was not excited, wherein the processor is configured to assign the non-selective HIS bundle capture to indicate that the corresponding one of the stimulus results in simultaneous capture of both the His bundle and the myocardium.

* * * * *